US011814698B2

United States Patent
Foley et al.

(10) Patent No.: US 11,814,698 B2
(45) Date of Patent: Nov. 14, 2023

(54) METHODS FOR SIMULTANEOUS LEACHING AND EXTRACTION OF PRECIOUS METALS

(71) Applicant: EXCIR WORKS CORP., Calgary (CA)

(72) Inventors: Stephen Foley, Saskatoon (CA); Hiwa Salimi, Saskatoon (CA); Loghman Moradi, Saskatoon (CA)

(73) Assignee: EXCIR WORKS CORP., Calgary (CA)

( * ) Notice: Subject to any disclaimer, the term of this patent is extended or adjusted under 35 U.S.C. 154(b) by 0 days.

(21) Appl. No.: 17/810,138

(22) Filed: Jun. 30, 2022

(65) Prior Publication Data

US 2022/0340998 A1    Oct. 27, 2022

Related U.S. Application Data

(63) Continuation of application No. 15/568,245, filed as application No. PCT/CA2016/050459 on Apr. 21, 2016, now Pat. No. 11,427,886.

(60) Provisional application No. 62/152,066, filed on Apr. 24, 2015, provisional application No. 62/150,513, filed on Apr. 21, 2015.

(51) Int. Cl.

| C22B 11/00 | (2006.01) |
|---|---|
| C22B 3/16 | (2006.01) |
| C22B 3/06 | (2006.01) |
| C22B 3/26 | (2006.01) |
| C22B 3/28 | (2006.01) |
| C22B 3/34 | (2006.01) |
| C22B 3/36 | (2006.01) |
| C22B 3/40 | (2006.01) |
| C22B 3/44 | (2006.01) |
| C07C 335/26 | (2006.01) |
| C07D 207/06 | (2006.01) |
| C07D 211/16 | (2006.01) |
| C07D 295/215 | (2006.01) |
| C22B 1/00 | (2006.01) |
| C25C 1/20 | (2006.01) |
| C25C 7/06 | (2006.01) |

(52) U.S. Cl.
CPC ............ *C22B 11/04* (2013.01); *C07C 335/26* (2013.01); *C07D 207/06* (2013.01); *C07D 211/16* (2013.01); *C07D 295/215* (2013.01); *C22B 1/00* (2013.01); *C22B 3/06* (2013.01); *C22B 3/16* (2013.01); *C22B 3/1608* (2013.01); *C22B 3/1616* (2013.01); *C22B 3/1625* (2013.01); *C22B 3/1666* (2013.01); *C22B 3/26* (2021.05); *C22B 3/28* (2021.05); *C22B 3/282* (2021.05); *C22B 3/284* (2021.05); *C22B 3/34* (2021.05); *C22B 3/36* (2021.05); *C22B 3/406* (2021.05); *C22B 3/44* (2013.01); *C25C 1/20* (2013.01); *C25C 7/06* (2013.01); *Y02P 10/20* (2015.11)

(58) Field of Classification Search
CPC ......... C22B 11/04; C22B 1/00; C22B 3/0005; C22B 3/0006; C22B 3/001–0013; C22B 3/06–10; C22B 3/16–1625; C22B 3/1666; C22B 3/44; C22B 3/0031; C22B 3/0035; C22B 3/0039; C07C 335/26; C07D 207/06; C07D 211/00; C07D 211/16; C07D 295/215; C25C 1/20; C25C 7/08
See application file for complete search history.

(56) References Cited

U.S. PATENT DOCUMENTS

| 4,684,404 | A | 8/1987 | Kalocsai |
|---|---|---|---|
| 4,919,716 | A | 4/1990 | Nakao et al. |
| 5,264,191 | A | 11/1993 | Nakao et al. |
| 5,389,124 | A | 2/1995 | Nakao |
| 5,607,619 | A | 3/1997 | Dadgar et al. |
| 5,981,788 | A | 11/1999 | Ofori et al. |
| 6,319,389 | B1 | 11/2001 | Fountain et al. |
| 11,408,053 | B2 | 8/2022 | Foley et al. |
| 11,427,886 | B2 | 8/2022 | Foley et al. |
| 2008/0261477 | A1 | 10/2008 | Nomura et al. |
| 2011/0028306 | A1 | 2/2011 | Variabel et al. |
| 2012/0228151 | A1* | 9/2012 | Moradi ............... C07D 211/14 548/953 |
| 2013/0276284 | A1 | 10/2013 | Brosseau et al. |
| 2016/0273060 | A1 | 9/2016 | Bobadilla Fazzini et al. |
| 2016/0362804 | A1 | 12/2016 | Chen et al. |
| 2018/0112289 | A1 | 4/2018 | Foley et al. |
| 2018/0142322 | A1 | 5/2018 | Foley et al. |

FOREIGN PATENT DOCUMENTS

| CA | 2597937 A1 | 8/2006 |
|---|---|---|
| CA | 2666767 A1 | 4/2008 |
| CA | 2739662 A1 | 4/2010 |

(Continued)

OTHER PUBLICATIONS

Vest et al, "Solvent extraction of gold with N-substituted benzoylthioureas" Fresenius J. of Anal. Chem., Sep. 1991, 341(9), pp. 566-568. (Year: 1991).*

"Basel Convention on the Control of Transboundary Movements of Hazardous Wastes and their Disposal," Environment. (1989). Retrieved from the Internet: https://treaties.un.org/Pages/ViewDetails.aspx?src=TREATY&mtdsg_no=XXVII-3&chapter=27&clang=_en. (13 pages).

(Continued)

*Primary Examiner* — Steven J Bos
(74) *Attorney, Agent, or Firm* — Clark & Elbing LLP

(57) ABSTRACT

The present application relates to methods for the simultaneous leaching and extraction of precious metals. For example, the present application relates to methods of leaching and extracting gold and/or palladium from a substance comprising gold and/or palladium such as a gold and/or palladium-containing ore in one step using a compound of Formula I: (I).

28 Claims, 3 Drawing Sheets

(56) References Cited

FOREIGN PATENT DOCUMENTS

| | | |
|---|---|---|
| CA | 2738692 A1 | 7/2010 |
| CA | 2821042 A1 | 6/2012 |
| CA | 2884363 A1 | 3/2014 |
| CA | 2940830 A1 | 9/2015 |
| CA | 2949036 A1 | 11/2015 |
| CN | 1635168 A | 7/2005 |
| CN | 101220173 A | 7/2008 |
| CN | 101230421 A | 7/2008 |
| CN | 101535510 A | 9/2009 |
| CN | 102952947 A | 3/2013 |
| CN | 103320620 A | 9/2013 |
| CN | 103857811 A | 6/2014 |
| CN | 104060095 A | 9/2014 |
| CN | 104263938 A | 1/2015 |
| EP | 0124213 A1 | 7/1984 |
| EP | 2226401 A1 | 9/2010 |
| EP | 2684622 A1 | 1/2014 |
| EP | 2765208 A1 | 8/2014 |
| GB | 1283389 A | 7/1972 |
| WO | WO-8200478 A1 | 2/1982 |
| WO | WO-2006013568 A2 | 2/2006 |
| WO | WO-2006084273 A2 | 8/2006 |
| WO | WO-2006087313 A1 | 8/2006 |
| WO | WO-2006087413 A1 | 8/2006 |
| WO | WO-2006119611 A1 | 11/2006 |
| WO | WO-2007042604 A1 | 4/2007 |
| WO | WO-2007045034 A1 | 4/2007 |
| WO | WO-2007053947 A1 | 5/2007 |
| WO | WO-2007074360 A2 | 7/2007 |
| WO | WO-2007109841 A1 | 10/2007 |
| WO | WO-2007115399 A1 | 10/2007 |
| WO | WO-2008017731 A1 | 2/2008 |
| WO | WO-2008047010 A2 | 4/2008 |
| WO | WO-2008059770 A1 | 5/2008 |
| WO | WO-2008139412 A1 | 11/2008 |
| WO | WO-2008141443 A1 | 11/2008 |
| WO | WO-2009017434 A1 | 2/2009 |
| WO | WO-2009037596 A2 | 3/2009 |
| WO | WO-2009050334 A1 | 4/2009 |
| WO | WO-2009067039 A1 | 5/2009 |
| WO | WO-2009068735 A1 | 6/2009 |
| WO | WO-2009069005 A2 | 6/2009 |
| WO | WO-2009105832 A1 | 9/2009 |
| WO | WO-2009114045 A1 | 9/2009 |
| WO | WO-2009120373 A2 | 10/2009 |
| WO | WO-2009130345 A1 | 10/2009 |
| WO | WO-2009153409 A1 | 12/2009 |
| WO | WO-2010036144 A1 | 4/2010 |
| WO | WO-2010037169 A1 | 4/2010 |
| WO | WO-2010076030 A1 | 7/2010 |
| WO | WO-2010080050 A1 | 7/2010 |
| WO | WO-2010084364 A1 | 7/2010 |
| WO | WO-2010094161 A1 | 8/2010 |
| WO | WO-2010121329 A1 | 10/2010 |
| WO | WO-2011015991 A2 | 2/2011 |
| WO | WO-2011047070 A1 | 4/2011 |
| WO | WO-2011059380 A1 | 5/2011 |
| WO | WO-2011091231 A1 | 7/2011 |
| WO | WO-2011100821 A1 | 8/2011 |
| WO | WO-2011130622 A1 | 10/2011 |
| WO | WO-2011154603 A1 | 12/2011 |
| WO | WO-2011154607 A1 | 12/2011 |
| WO | WO-2011161597 A1 | 12/2011 |
| WO | WO-2012027532 A2 | 3/2012 |
| WO | WO-2012071342 A2 | 5/2012 |
| WO | WO-2012076981 A1 | 6/2012 |
| WO | WO-2012078019 A2 | 6/2012 |
| WO | WO-2012078020 A2 | 6/2012 |
| WO | WO-2012079129 A1 | 6/2012 |
| WO | WO-2012114165 A1 | 8/2012 |
| WO | WO-2012122774 A1 | 9/2012 |
| WO | WO-2012141607 A1 | 10/2012 |
| WO | WO-2012149631 A1 | 11/2012 |
| WO | WO-2012168915 A1 | 12/2012 |
| WO | WO-2012171480 A1 | 12/2012 |
| WO | WO-2012171481 A1 | 12/2012 |
| WO | WO-2012174349 A2 | 12/2012 |
| WO | WO-2013001365 A2 | 1/2013 |
| WO | WO-2013030450 A1 | 3/2013 |
| WO | WO-2013051715 A1 | 4/2013 |
| WO | WO-2013082614 A1 | 6/2013 |
| WO | WO-2013090517 A1 | 6/2013 |
| WO | WO-2013152424 A1 | 10/2013 |
| WO | WO-2014009928 A1 | 1/2014 |
| WO | WO-2014022946 A1 | 2/2014 |
| WO | WO-2014029017 A1 | 2/2014 |
| WO | WO-2014042131 A1 | 3/2014 |
| WO | WO-2014056034 A1 | 4/2014 |
| WO | WO-2014114746 A1 | 7/2014 |
| WO | WO-2014121150 A1 | 8/2014 |
| WO | WO-2014170863 A1 | 10/2014 |
| WO | WO-2014177765 A1 | 11/2014 |
| WO | WO-2014195586 A1 | 12/2014 |
| WO | WO-2015031943 A1 | 3/2015 |
| WO | WO-2015049421 A1 | 4/2015 |
| WO | WO-2015052658 A1 | 4/2015 |
| WO | WO-2015075502 A1 | 5/2015 |
| WO | WO-2015102865 A1 | 7/2015 |
| WO | WO-2015102867 A1 | 7/2015 |
| WO | WO-2015121799 A1 | 8/2015 |
| WO | WO-2015129385 A1 | 9/2015 |
| WO | WO-2015130607 A1 | 9/2015 |
| WO | WO-2015147330 A1 | 10/2015 |
| WO | WO-2015172175 A1 | 11/2015 |
| WO | WO-2015178752 A1 | 11/2015 |
| WO | WO-2015181446 A1 | 12/2015 |
| WO | WO-2016008932 A1 | 1/2016 |
| WO | WO-2016168930 A1 | 10/2016 |
| WO | WO-2016168933 A1 | 10/2016 |

OTHER PUBLICATIONS

"Canada: Light-Duty: Emissions, " Transport Policy. (11 pages). Retrieval date: Jan. 13, 2020, Retrieved from the Internet: https://www.transportpolicy.net/standard/canada-light-duty-emissions/.

"Cars and Light-Duty Trucks: Tier 3," DieselNet: Emission Standards. retrieved on Jan. 6, 2020 from https://dieselnet.com/standards/us/ld_t3.php (9 pages).

"Columbus Metallurgical Complex," Sibanye Stillwater, retrieved on Jan. 13, 2020 from https://www.sibanyestillwater.com/business/americas/pgm-operations-americas/columbus-metallurgical-complex/. (11 pages).

"Copper—Element information, properties and uses," Royal Society of Chemistry. Retrieved on Sep. 23, 2020 from <https://www.rsc.org/periodic-table/element/29/copper> (4 pages).

"Copper Facts", Government of Canada. Retrieved on Sep. 23, 2020 from <https://www.nrcan.gc.ca/our-natural-resources/minerals-mining/minerals-metals-facts/copper-facts/20506> (8 pages).

"Cyanide Use in Gold Mining," Earthworks. Retrieved on Feb. 3, 2020 from the https://www.earthworks.org/issues/cyanide/. (3 pages).

"Electrical/Electronic Waste and Children's Health DRAFT," E-waste and Children's Health, World Health Organization. (2015) (43 pages), retrieved from https://www.who.int/ceh/capacity/eWaste_and_childrens_health_DRAFT.pdf.

"Electronic Recyclers International: Current Member Spotlight," NERC. Retrieved from <https://nerc.org/advisory-members/member-spotlight/2015/03/electronic-recycling-international-(eri)>. (9 pages).

"End of Life Vehicles," European Commission. Retrieved on Jan. 9, 2020 from <https://ec.europa.eu/environment/waste/elv/index.htm> (2 pages).

"European Union Risk Assessment Report: 2,2',6,6'-TetrabTomo-4,4'-Isopropylidenediphenol (Tetrabromobisphenol-A or TBBP-A) Part II—Human Health," European Commission Joint Research Centre. 63:1-157 (2006) (170 pages).

"Gold Properties," BullionVault. Retrieved on Feb. 11, 2020 from <https://www.bullionvault.com/gold-guide/gold-properties> (4 pages).

"Gold Supply," World Gold Council, retrieved on Feb. 11, 2020 from <https://www.gold.org/about-gold/gold-supply> (2 pages).

(56) References Cited

OTHER PUBLICATIONS

"Mining in Canada," The Canadian Minerals and Master Plan. Retrieved on Jan. 6, 2020 from <https://www.minescanada.ca/en/content/mining-canada-0> (12 pages).
"The Social and Economic Impacts of Gold Mining", World Gold Council, Mar. 2015, 40 pages.
"Total Vehicle Sales," FRED Economic Data 2020, Retrieved on Jan. 14, 2020 from<https://fred.stlouisfed.org/series/TOTALSA#0> (1 page).
"Utilization and Fields of Application of Gold", Gold.info, Retrieved on Feb. 11, 2020 from <https://www.gold.info/en/application-of-gold/> (3 pages).
"Waste from Electrical and Electronic Equipment (WEEE)," European Commission. retrieved on Feb. 3, 2020, from <http://ec.europa.eu/environment/waste/weee/legis_en.htm> (5 pages).
"What Is An End Of Life Vehicle", Green Vehicle. Retrieved on Jan. 9, 2020 from <https://greenvehicledisposal.com/what-is-an-end-of-life-vehicle/#:~:text=In%20the%20United%20States%2010,vehicles%20yearly%20in%20Ontario%20alone> (4 pages).
'How much copper is there and where does it come from?, European Copper Institute, Copper Alliance. retrieved on Sep. 23, 2020 from <https://copperalliance.eu/about-copper/copper-and-its-alloys/resources/> (3 pages).
Aberasturi et al., "Recovery by Hydrometallurgical Extraction of the Platinum-Group Metals from Car Catalytic Converters," Minerals Engineering, 2011, vol. 24, pp. 505-513.
Amey, "Gold," U.S. Geological Survey Minerals Yearbook. 32.1-32.13 (2003).
Antrekowitsch et al., "Metallurgical Recycling of Electronic Scrap," TMS. pp. 899-908 (2009).
Banhegyi, "What is the difference between compatibilizer and coupling agents for polymer composites?," ResearchGate, <https://www.researchgate.net/post/What_is_the_difference_between_compatibilizer_and_coupling_agents_for_polymer_composites/5454f1b2d3df3e59708b45a4/citation/download/>, dated Nov. 1, 2014 (1 page).
Birak et al., "Dense Nonaqueous Phase Liquids at Former Manufactured Gas Plants: Challenges to Modeling and Remediation," available in PMC Apr. 1, 2010, published in final edited form as: J Contam Hydrol. 105:81-98 (2009) (37 pages).
Chapter 3: Production and Uses of Platinum Group Metals, International Platinum Group Metals Association. Retrieval on Jan. 6, 2020 from <https://ipa-news.de/assets/sustainability/IPA_Guidance/Chapter3_PGM_Guide.pdf> (10 pages).
Chinese Patent Application No. CN201680036516, Office Action dated Sep. 28, 2020—English Translation Available (16 pages).
Communication Pursuant to Article 94(3) EPC for European Patent Application No. 16782430.9, dated Mar. 31, 2022 (5 pages).
Condra, "Future Of E-Waste In The Circular Economy", human-I-T. Retrieved on May 15, 2020 from https://www.human-i-t.org/blogs/the-future-of-e-waste-in-the-circular-economy (3 pages).
Cooper and Beecham., "A Study of Platinum Group Metals in Three-Way Autocatalysts," Platinum Metals Review, 2013, vol. 57,(4), pp. 281-288.
Corrected Notice of Allowability for U.S. Appl. No. 15/568,245, dated Feb. 16, 2022 (2 pages).
Crundwell et al., "Extractive Metallurgy of Nickel, Cobalt and Platinum Group Metals," Elsevier, 2011, 624 pages.
Crundwell et al., "Extractive Metallurgy of Nickel, Cobalt and Platinum-Group Metals," Elsevier, 2011, 583 pages.
Cui and Forssberg., "Mechanical Recycling of Waste Electric and Electronic Equipment: A Review", Journal of Hazardous Materials, 2003, vol. 99(3), pp. 243-263.
Dalrymple et al., "An Integrated Approach to Electronic Waste (WEEE) Recycling", Circuit World, 2007, vol. 33(2), pp. 52-58.
Deveci et al., "Extraction of Copper from Scrap TV Boards by Sulphuric Acid Leaching Under Oxidising Conditions," Conference Paper Jan. 2010, 8 pages.

Environment, The Conference Board Of Canada, Apr. 2016, 17 pages. Retrieved from the internet: https://www.conferenceboard.ca/hcp/provincial/environment.aspx?AspxAutoDetectCookieSupport=1.
Foley., "Sustainable Technique Recovers Gold From E-waste Cheaply", University of Saskatchewan, Feb. 3, 2016. [Retreieved Feb. 3, 2020]. Retrieved from the internet: https://phys.org/news/2016-02-sustainable-technique-recovers-gold-e-waste.html.
Fornalczyk and Saternus., "Removal of Platinum Group Metals From the Used Auto Catalytic Converter," Matelurgija, 2009, vol. 48(2), pp. 133-136.
Friedrich, "Chapter 1: Routes for achieving multifunctionality in reinforced polymers and composite structures", *Multifunctionality of Polymer Composites*. Elsevier, 3-41 (2015).
Gdoutos, *Fracture Mechanics: An Introduction, Second Edition*. Springer, 1-369 (2005) (391 pages).
George, "Gold," U.S. Geological Survey Minerals Yearbook. 32.1-32.13 (2004).
Guo et al., "Performance and Thermal Behavior of Wood Plastic Composite Produced by Nonmetals of Pulverized Waste Printed Circuit Boards," Journal of Hazardous Materials. 179(1-3):203-207 (2010).
Habashi et al., Principles of Extractive Metallurgy, New York: Gordon and Breach, 1980, vol. 1, 2nd edition, pp. 39.
Habashi et al., Principles of Extractive Metallurgy, New York: Gordon and Breach, 1980, vol. 2, 2nd edition, pp. 39.
Habashi et al., Principles of Extractive Metallurgy, New York: Gordon and Breach, 1980, vol. 3, 2nd edition, pp. 39.
Hageluken., "Closing the Loop—Recycling of Automotive Catalysts," Metall, Jan. 2011, vol. 61(1-2), pp. 24-39.
Hageluken., "Recycling the Platinum Group Metals: A European Perspective," Platinum Metals Review, 2012, vol. 66(1), 29-35 (7 pages).
Herat, "Environmental Impacts and Use of Brominated Flame Retardants in Electrical and Electronic Equipment," The Environmentalist. 28(4): (2008) (31 pages).
Indian Patent Application No. 201717040510, Examination Report dated Feb. 22, 2021 (7 pages).
International Preliminary Report on Patentability for International Patent Application No. PCT/CA2016/050459, dated Oct. 24, 2017 (7 pages).
International Preliminary Report on Patentability for International Patent Application No. PCT/CA2016/050463, dated Oct. 24, 2017 (8 pages).
International Search Report and Written Opinion for International Patent Application No. PCT/CA2021/051102, dated Nov. 22, 2021 (13 pages).
International Search Report and Written Opinion for International Patent Application No. PCT/CA2021/051351, dated Dec. 20, 2021 (13 pages).
International Search Report and Written Opinion for International Patent Application No. PCT/CA2021/051385, dated Dec. 15, 2021 (15 pages).
Japanese Patent Application No. JP20170555706, Decision to Grant dated Feb. 16, 2021—English Translation not available (2 pages).
Japanese Patent Application No. JP20170555706, Office Action dated Sep. 14, 2020 (English Translation Available) (3 pages).
Johnson Matthey, Retrieved on Jan. 13, 2020 from <https://matthey.com/en> (1 page).
Khaliq et al., "Metal Extraction Processes for Electronic Waste and Existing Industrial Routes: A Review and Australian Perspective," Resources 2014, vol. 3, pp. 152-179.
Maps and Data—U.S. Plug-in Electric Vehicle Sales by Model, Alternative Fuel Data Center, 2020, Retrieved on Jan. 13, 2020, from <https://afdc.energy.gov/data/10567> (1 page).
MAVERICK., "China Creates $16-Billion Silk Road Gold Fund", Wallstreet Daily. (2015). Retrieved from <https://www.wallstreetdaily.com/2015/06/14/china-silk-road-gold-fund/> (1 page).
Monitour, E-Trash Transparency Project, MIT. (May 2016). Retrieved from <http://senseable.mit.edu/monitour-app> (1 page).
Non-Final Office Action for U.S. Appl. No. 15/568,230, dated Apr. 6, 2021 (27 pages).

(56) References Cited

OTHER PUBLICATIONS

Notice of Allowance for U.S. Appl. No. 15/568,245, dated Aug. 25, 2021 (7 pages).
Notice of Allowance for U.S. Appl. No. 15/568,245, dated Apr. 28, 2021 (25 pages).
Notice of Allowance for U.S. Appl. No. 15/568,245, dated Dec. 16, 2021 (7 pages).
Notice of Allowance for U.S. Appl. No. 15/568,245, dated Mar. 30, 2022 (5 pages).
Notice of Allowance for U.S. Appl. No. 15/568,230, dated Dec. 20, 2021 (8 pages).
Notice of Allowance for U.S. Appl. No. 15/568,230, dated Mar. 30, 2022 (6 pages).
Notice of Allowance for U.S. Appl. No. 15/568,230, dated Sep. 15, 2021 (6 pages).
Notice of Completing Formalities for Patent Registration for Chinese Patent Application No. 201680036516.9, dated Jul. 30, 2021 (4 pages).
Office Action for Canadian Patent Application No. 2983350, dated Mar. 2, 2022 (4 pages).
Office Action for Canadian Patent Application No. 2983353, dated Mar. 3, 2022 (5 pages).
Office Action for Chinese Patent Application No. 201680036516.9, dated Mar. 31, 2021 (4 pages).
Office Action for Chinese Patent Application No. CN201680036516, dated Mar. 31, 2021 (English Translation Available).
International Search Report and Written Opinion for International Patent Application No. PCT/CA2016/050463, dated Aug. 29, 2016 (11 pages).
Office Action for Japanese Patent Application No. 2021-070523, dated Feb. 3, 2022 (2 pages).
Oraby et al., "The Selective Leaching of Copper From a Gold-copper Concentrate in Glycine Solutions," Hydrometallurgy. 150:14-19 (2014).
Petter et al., "Evaluation of Gold and Silver Leaching From Printed Circuit Board of Cellphones," Waste Management, 2014, vol. 34, pp. 475-482.
Recycling Rates of Metals: A Status Report, International Resource Panel, May 2011, 48 pages.
Schulzke, "John Shegerian—CEO of Electronic Recyclers International," (2012), retrieved from: https://ideamensch.com/john-shegerian/. (10 pages).
Screen captures from video clip entitled "Technology With a Heart of Recycled Gold", Dell. Retrieved Feb. 3, 2020 from <https://www.dell.com/learn/us/en/uscorp1/videos~en/documents~gold-bayou.aspx?c=us&l=en&s=corp&cs=uscorp1> (2 pages).
Sharizan, I., "Gold leaching process and recovery from goldscraps using ascorbic acid:, Universiti Malaysia Perlis, School of Materials Engineering, 2010, Perlis Malaysia. (24 pages). Retrieved from the Internet: ."title="Link: http://dspace.unimap.edu.my/xmlui/bitstream/123456789/12930/1/p.+1-24.pdf>.">http://dspace.unimap.edu.my/xmlui/bitstream/123456789/12930/1/p.+1-24.pdf.
Shuey and Taylor., "Review of Pyrometallurgical Treatment of Electronic Scrap," Mining Engineering, Apr. 2005, vol. 57(4), pp. 67-70.
Tulumba, "Overall U.S. Auto Industry Sales Figures," Good Car Bad Car, <https://www.goodcarbadcar.net/usa-auto-industry-total-sales-figures/>, retrieved on Jan. 13, 2020 (1 page).
Notice of Allowance for U.S. Appl. No. 15/568,245, dated Jan. 6, 2021 (7 pages).
Vest et al., "Solvent extraction of gold with N-substituted benzoylthioureas," Fresenius J Anal Chem. 341(9):566-8 (Sep. 1991).
Yoo and Lee., "Leaching of Copper and Silver From Ground Mobile Phone Printed Circuit Boards Using Nitric Acid," Journal of the Korean Institute of Resources Recycling, Jan. 2008, vol. 17(3), pp. 48-55.
Zhang et al., "Removal of brominated flame retardant from electrical and electronic waste plastic by solvothermal technique," J Hazard Mater. 221-222:193-198 (2012).
Akcil et al., "Precious Metal Recovery From Waste Printed Circuit Boards Using Cyanide and Non-Cyanide Lixiviants—A Review," Waste Management, Nov. 2015, vol. 45, pp. 258-271.
Alzate et al., "Recovery of Gold From Waste Electrical and Electronic Equipment (WEEE) Using Ammonium Persulfate," Waste Management, Nov. 2016, pp. 1-8.
Anonymous, "Gold," Mining Journal, Jun. 11, 2004, pp. 19-24.
Aylmore et al., "Thiosulfate Leaching of Gold—A Review," Minerals Engineering, Feb. 2001, vol. 14(2), pp. 135-174.
Barbieri et al., "A New Environmentally Friendly Process for the Recovery of Gold From Electronic Waste," Environmental Chemistry Letters, 2010, vol. 8, pp. 171-178.
Berzowsky et al., "Recovery of Gold and Silver from Oxidation Leach Residues by Ammoniacal Thiosulfate Leaching," Presented at the 108th AIME Annual Meeting, New Orleans, Louisiana, Feb. 18-22, 1979, pp. 1-17.
Breuer et al., "The Reduction of Copper(li) and the Oxidation of Thiosulfate and Oxysulfur Anions in Gold Leaching Solutions," Hydrometallurgy, Jul. 2003, vol. 70(1-3), pp. 163-173.
Cayumil et al., "Concentration of Precious Metals During Their Recovery From Electronic Waste," Waste Management, Dec. 2015, pp. 1-10.
Chandra and Jeffrey., "A Fundamental Study of Ferric Oxalate for Dissolving Gold in Thiosulfate Solutions," Hydrometallurgy, Jun. 2005, vol. 77(3-4), pp. 191-201.
Chatterjee et al., "Efficient Management of E-Wastes," International Journal of Environmental Science and Technology, Jul. 2016 (12 pages).
Chehade et al., "Recovery of Gold, Silver, Palladium, and Copper from Waste Printed Circuit Boards," International Conference on Chemical, Civil and Environment Engineering, 2012, pp. 226-234.
Cheng et al., "Fast and Effective Gold Leaching from a Desulfurized Gold Ore Using Acidic Sodium Chlorate Solution at Low Temperature," Industrial & Engineering Chemistry Research, Nov. 2013, vol. 52, pp. 16622-16629.
Chmielewski et al., "Separation Technologies for Metals Recovery From Industrial Wastes," Hydrometallurgy, 1997, vol. 45, pp. 333-344.
Dai et al., "Modeling the Equilibrium Loading of Gold Onto Activated Carbon From Complex Cyanide Solutions," Mining, Metallurgy & Exploration, Nov. 2010, vol. 27(4), pp. 190-195.
Deschenes et al., "Effect of Oxygen and Lead Nitrate on the Cyanidation of a Sulphide Bearing Gold Ore," Minerals Engineering, Aug. 1995, vol. 8(8), pp. 923-931.
Doidge et al., "A Simple Primary Amide for the Selective Recovery of Gold from Secondary Resources," Angewandte Chemie International Edition, Sep. 2016, vol. 55, pp. 12436-12439.
Feng et al., "Ammoniacal Thiosulphate Leaching of Gold in the Presence of Pyrite," Hydrometallurgy, Aug. 2006, vol. 82(3-4), pp. 126-132.
Filmer et al., "A Comparison of Cyanide, Thiourea, and Chlorine as Lixiviants for Gold. Gold Mining, Metallurgy and Geology," Australasian Institute of Mining and Metallurgy, Melbourne, 1984, pp. 279-287.
Finkelstein et al., "An Aqueous Chlorination Process for the Treatment of Merrill Slimes and Gravity Concentrates From Gold Ores," Journal of the South African Institute of Mining and Metallurgy, Dec. 1966, vol. 67, pp. 196-215.
Geoffroy et al., "A Method for Leaching or Dissolving Gold From Ores or Precious Metal Scrap," The Journal of the Minerals, Aug. 2005, vol. 57(8), pp. 47-50.
Ghasem et al., "The Extraction of Gold from E-waste by Hydrometallurgy," Oriental Journal of Chemistry, Mar. 2015, vol. 31(1), pp. 113-120.
Gill et al., "New Leaching Agents for Oxides. The Reaction of Metal Oxides With the Mixed Non-Aqeous Systems Dimethyl Sulphoxide-sulphur Dioxide, Dimethyl Formamide-Sulphur Dioxide and Acetonitrile-Sulphur Dioxide," Hydrometallurgy, Dec. 1984, vol. 13(2), pp. 221-226.
Gonen., "Leaching of Finely Disseminated Gold Ore With Cyanide and Thiourea Solutions," Hydrometallurgy, Apr. 2003, vol. 69(1-3), pp. 169-176.

(56) References Cited

OTHER PUBLICATIONS

Groenewald., "The Dissolution of Gold in Acidic Solutions of Thiourea," Hydrometallurgy, Feb. 1976, vol. 1(3), pp. 277-290.
Grosse et al., "Leaching and Recovery of Gold Using Ammoniacal Thiosulfate Leach Liquors (a Review)," Hydrometallurgy, Apr. 2003, vol. 69(1-3), pp. 1-21.
Grosvenor et al., "New Interpretations of XPS Spectra of Nickel Metal and Oxides," Surface Science, 2006, vol. 600, pp. 1771-1779.
Gurung et al., "Recovery of Gold and Silver From Spent Mobile Phones by Means of Acidothiourea Leaching Followed by Adsorption Using Biosorbent Prepared From Persimmon Tannin," Hydrometallurgy, 2013, vol. 133, pp. 84-93.
Habashi et al., "A Textbook of Hydrometallurgy," Metallurgie Extractive Quebec: 2 edition. pp. 248-350 (Jul. 1999).
Hageluken., "Improving Metal Returns and Eco-Efficiency in Electronics Recycling," IEEE, 2006, pp. 218-223.
Hageluken., "Recycling of Electronic Scrap at Umicore's Integrated Metals Smelter and Refinery," World of Metallurgy—Erzmetall, May 2006, vol. 59(3), pp. 152-161.
Hasab et al., "Chloride-Hypochlorite Leaching of Gold From a Mechanically Activated Refractory Sulfide Concentrate," Hydrometallurgy, Jun. 2013, vol. 138, pp. 59-64.
Hasab et al., "Simultaneous Sulfide Oxidation and Gold Leaching of a Refractory Gold Concentrate by Chloride-Hypochlorite Solution," Minerals Engineering, 2013, vol. 50-51, pp. 140-142.
He and Xu., "Recycling Gold and Copper From Waste Printed Circuit Boards Using Chlorination Process," The Royal Society of Chemistry, Sep. 2015, vol. 5, pp. 8957-8964.
Hewitt et al., "The Ups and Downs of Gold Recycling Understanding Market Drivers and Industry Challenges," Boston Consulting Group, Mar. 2015, pp. 1-17.
Ikiz et al., "Dissolution Kinetics of Primary Chalcopyrite Ore in Hypochlorite Solution," Minerals Engineering, Jul. 2006, vol. 19(9), pp. 972-974.
Imrelucaci et al., "Technical and Environmental Assessment of Gold Recovery From Secondary Streams Obtained in the Processing of Waste Printed Circuit Boards," Chemical Engineering Journal, Oct. 2016, pp. 1-22.
Jadhav and Hocheng., "Hydrometallurgical Recovery of Metals from Large Printed Circuit Board Pieces," Scientific Reports, Sep. 2015, pp. 1-9.
Jeffrey et al., "A Kinetic Study That Compares the Leaching of Gold in the Cyanide, Thiosulfate, and Chloride Systems," Metallurgical and Materials Transactions B 32, Dec. 2001, vol. 32(6), pp. 979-986.
Jeffrey et al., "The Importance of Controlling Oxygen Addition During the Thiosulfate Leaching of Gold Ores," International Journal of Mineral Processing, Sep. 29, 2003, vol. 72(1-4), pp. 323-330.
Jiang et al., "Environmentally Benign Solution for Recycling Electronic Waste Using the Principles of Green Chemistry," Advanced Materials Research, 2014, vol. 878, pp. 406-412.
Jiang et al., "Improving the End-of-Life for Electronic Materials via Sustainable Recycling Methods," Procedia Environmental Sciences, 2012, vol. 16, pp. 485-490.
Jiang et al., Inorganic Chemistry, 2001, vol. 17 (3), pp. 343-348.
Jing Ying et al., "Thiourea Leaching Gold and Silver From the Printed Circuit Boards of Waste Mobile Phones," Waste Management, 2012, vol. 32, pp. 1209-1212.
Jujun et al., "A New Strain for Recovering Precious Metals From Waste Printed Circuit Boards," Waste Management, 2014, vol. 34, pp. 901-907.
Karamanoglu et al., "An Economic Analysis of the Recovery of Gold From CPU, Boards, and Connectors Using Aqua Regia," Desalination and Water Treatment, Feb. 2016, vol. 57, pp. 2570-2575.
Kaya., "Recovery of Metals and Nonmetals From Electronic Waste by Physical and Chemical Recycling Processes," Waste Management, Aug. 2016, vol. 57, pp. 64-90.
Kazakov et al., "Redox Potential of the Gold(I) Thiourea Complex," Russian Journal of Inorganic Chemistry, 1964, vol. 9 (5), pp. 708-709.
Keller., "Assessment of Gold Recovery Processes in Bangalore, India and Evaluation of an Alternative Recycling Path for Printed Wiring Boards," Swiss Federal Institute of Technology Zurich, Oct. 2006, pp. 1-105.
Kim et al., "Selective Recovery of Gold From Waste Mobile Phone PCBs by Hydrometallurgical Process," Journal of Hazardous Materials, Journal of Hazardous Materials, 2011, vol. 198, pp. 206-215.
Kondos et al., "Process Optimization Studies in Gold Cyanidation," Hydrometallurgy, Oct. 1995, vol. 39(1-3), pp. 235-250.
Korzenski., "A Sustainable Approach to Dealing with Electronic Waste," Evolv the Cleantech Solution to Waste. vol. 36 (2002) (41 pages).
Krzewska and Podsiadly., "Silver-Silver Thiourea Electrode for Determination of Free Thiourea Concentration in HClO4 Medium," Journal of Inorganic and Nuclear Chemistry, 1980, vol. 42, pp. 83-86.
Kumar et al., "Leaching of Metals From Waste Printed Circuit Boards (WPCBs) Using Sulfuric and Nitric Acids," Environmental Engineering and Management Journal, Oct. 2014, vol. 13(10), pp. 2601-2607.
Kumari et al., "Clean Process for Recovery of Metals and Recycling of Acid From the Leach Liquor of PCBs," Journal of Cleaner Production. vol. 395, pp. 1-9 (2015).
Lee et al., "A Study on the Recycling of Scrap Integrated Circuits by Leaching," Waste Management & Research, Jul. 2010, vol. 29(7), pp. 677-685.
Lekka et al., "Gold Recovery From Waste Electrical and Electronic Equipment by Electrodeposition: A Feasibility Study," Hydrometallurgy, Jul. 2015, vol. 157, pp. 97-106.
Leung et al., "Confronting a Toxic Blowback From the Electronics Trade," American Association for the Advancement of Science, Aug. 28, 2009, vol. 325, p. 1055.
Li et al., "A Review of Gold Leaching in Acid Thiourea Solutions," Mineral Processing and Extractive Metallurgy Review, Sep. 2006, vol. 27(3), pp. 177-214.
Li et al., "Thiocyanate Hydrometallurgy for the Recovery of Gold Part II: The Leaching Kinetics," Hydrometallurgy, Feb. 2012, vol. 113-114, pp. 10-18.
Lin et al., "Organic Aqua Regia-Powerful Liquids for Dissolving Noble Metals," Angewandte Chemie International Edition, Oct. 2010, vol. 49(43), pp. 7929-7932.
Liu and Yen., "Effects of Sulphide Minerals and Dissolved Oxygen on the Gold and Silver Dissolution in Cyanide Solution," Minerals Engineering, Jan.-Feb. 1995, vol. 8(1-2), pp. 111-123.
Lu and Xu., "Precious Metals Recovery From Waste Printed Circuit Boards: A Review for Current Status and Perspective," Resources, Conservation and Recycling, May 2016, vol. 113, pp. 28-39.
Mardsen and House., "The Chemistry of Gold Extraction," Society for Mining, Metallurgy, and Exploration, Inc., 2006, West Sussex, England (682 pages).
Mecucci et al., "Leaching and Electrochemical Recovery of Copper, Lead and Tin From Scrap Printed Circuit Boards," Journal of Chemical Technology and Biotechnology, 2002, vol. 77, pp. 449-457.
Mellor et al., "A Comprehensive Treatise on Inorganic and Theoretical Chemistry," Longmans, Green and Company, 1923, vol. 3, pp. 498-500.
Munoz et al., "Noncyanide Leaching of an Auriferous Pyrite Ore From Ecuador," Minerals and Metallurgical Processing, 2000, vol. 17, pp. 198-204.
Nakao et al., "Reversible Dissolution/Deposition of Gold in Iodine-Iodide-Acetonitrile Systems," Chemical Communication, 1996, vol. 8, pp. 897-898.
Nam et al., "Use of Chloride-Hypochlorite Leachants to Recover Gold From Tailing," International Journal of Mineral Processing, Mar. 28, 2008, vol. 86(1-4), pp. 131-140.
Namias., "The Future of Electronic Waste Recycling in the United States: Obstacles and Domestic Solutions," Earth Engineering Center, Jul. 2013, pp. 1-51.

(56) References Cited

OTHER PUBLICATIONS

Nesbitt et al., "Determination of the Mechanism of the Chlorination of Gold in Aqueous Solutions," Industrial & Engineering Chemistry Research, Aug. 1990, vol. 29(8), pp. 1696-1700.
Oguchi et al., "Fate of Metals Contained in Waste Electrical and Electronic Equipment in a Municipal Waste Treatment Process," Waste Management, 2012, vol. 32, pp. 96-103.
Orgul and Atalay., "Reaction Chemistry of Gold Leaching in Thiourea Solution for a Turkish Gold Ore," Hydrometallurgy, Dec. 2002, vol. 67(1-3), pp. 71-77.
Owens., "Extreme Prospects High Gold Prices Are Making It Worthwhile to Look for Gold in Some Unusual Places," Nature, Mar. 14, 2013, vol. 495, pp. S4-S6.
Park and Fray., "Recovery of High Purity Precious Metals From Printed Circuit Boards," Journal of Hazardous Materials, 2009, vol. 164, pp. 1152-1158.
Parker et al., "An Application of Acetonitrile Leaching and Disproportionation Refining Segregated Copper From Roasted Concentrates and Ores," Hydrometallurgy, Aug. 1981, vol. 7(3), pp. 213-233.
Plaskin et al., "Dissolution of Gold and Silver in Solutions of Thiourea Sbornik Nauchnyhk Trudov," Institut Tsvetnykh Metallov, vol. 33, pp. 107-119.
Plessers., "Economic and Environmental Assessment and Optimization of Recycling Scenarios for IT Equipment in Developing Countries," KU Leuven Faculty of Engineering Science, 2012-2013, pp. 1-103.
Preisler et al., "Oxidation-Reduction Potentials of Thiol-Dithio Systems Thiourea-Formamidine Disulfide," Journal of the American Chemical Society, Feb. 1947, vol. 69(2), pp. 322-325.
Quinet et al., "Recovery of Precious Metals From Electronic Scrap by Hydrometallurgical Processing Routes," Minerals and Metallurgical Processing, 2005, vol. 22 (1), p. 17.
Rabai and Epstein., "Systematic Design of Chemical Oscillators 83 Equilibria and Kinetics of the Fast Interaction Between Copper(II) and Thiosulfate Ions in Aqueous Solution," Inorganic Chemistry, Jul. 1992, vol. 31(15), pp. 3239-3242.
Ritchie et al., "Are There Realistic Alternatives to Cyanide as a Lixiviant For Gold at the Present Time," Cyanide: Social, Industrial and Economic Aspects, TMS, Warrendale, 2001, pp. 427-440.
Saadatjoo et al., "Recovery of Gold From Computer Circuit Board Scraps: The Study of the Effect of Different Reductants," Journal of Applied Chemistry, 2013, vol. 8(27), pp. 55-60.
Sahin et al., "A Potential Alternative for Precious Metal Recovery from E-waste: Iodine Leaching," Separation Science and Technology, Jun. 2015, vol. 50, pp. 2587-2595.
Sceresini., "Gold-Copper Ores," Elsevier Developments in Mineral Processing, 2005, vol. 15, pp. 789-824.
Schulze., "New Aspects in Thiourea Leaching of Precious Metals," Journal of Metals, Jun. 1984, vol. 36(6), pp. 62-65.
Senanayake., "Gold Leaching in Non-Cyanide Lixiviant Systems: Critical Issues on Fundamentals and Applications," Minerals Engineering, Jun. 2004, vol. 179(6), pp. 785-801.
Sheng et al., "Recovery of Gold From Computer Circuit Board Scrap Using Aqua Regia, " Waste Management & Research, 2007, vol. 25, pp. 380-383.
Veit et al., "Recovery of Copper From Printed Circuit Boards Scraps by Mechanical Processing and Electrometallurgy," Journal of Hazardous Materials, 2006, vol. B137, pp. 1704-1709.
Yoshimura et al., "Novel Process for Recycling Gold From Secondary Sources: Leaching of Gold by Dimethyl Sulfoxide Solutions Containing Copper Bromide and Precipitation With Water," Hydrometallurgy, Oct. 2014, vol. 149, pp. 177-182.
Zhang and Xu., "A Review of Current Progress of Recycling Technologies for Metals From Waste Electrical and Electronic Equipment," Journal of Cleaner Production, Apr. 2016, vol. 127, pp. 19-36.
Zhang et al., "A Study of the Gold Colloid Dissolution Kinetics in Oxygenated Ammoniacal Thiosulfate Solutions," Hydrometallurgy, 2004, vol. 74, pp. 243-257.
Zhang et al., "An Electrochemical Study of the Dissolution of Gold in Thiosulfate Solutions Part I: Alkaline Solutions," Journal of Applied Electrochemistry, 2003, vol. 33, pp. 767-775.
Chinese Patent Application No. CN20168036516, Office Action dated Feb. 25, 2020 (English Translation Available) (18 pages).
Dominguez et al., "Liquid-Liquid Extraction of Palladium(II) and Gold(III) with N-benzoyl-N',N'-diethylthiourea and the Synthesis of a Palladium Benzoylthiourea Complex," Polyhedron, Jun. 2002, vol. 21 (14-15), pp. 1429-1437.
Communication Pursuant to Article 94(3) EPC for European Patent Application No. 16782430.9, dated Apr. 30, 2020 (5 pages).
European Patent Application No. 16782430.9, Extended European Search Report dated Dec. 14, 2018 (8 pages).
Japanese Patent Application No. JP20170555706, Office Action dated Feb. 14, 2020 (English Translation Available) (5 pages).
Oraby et al., "The Leaching of Gold, Silver and Their Alloys in Alkaline Glycine-peroxide Solutions and Their Adsorption on Carbon," Hydrometallurgy, Feb. 2015, vol. 152, pp. 199-203.
Nakao., "Dissolution of Noble Metals in Halogen-Halide-Polar Organic Solvent Systems," Journal of the Chemical Society, Chemical Communications, 1992, vol. 5, pp. 426-427.
University of Saskatchewan., "Turning Electronic Waste into Gold," Science 1, 26, 32, 37 and 39-44 Daily® website, Jan. 28, 2016.
Cui., et al., "Metallurgical Recovery of Metals From Electronic Waste: A Review," Journal of Hazardous Materials, Oct. 2008, vol. 158 (2-3), pp. 228-256.
Avraamides et al., "Leaching of Silver with Copper (II) Ions in Aqueous Acetonitrile Solutions: Solubility of Salts and Equilibrium Constant Measurements in Sulphate Media," Hydrometallurgy, Mar. 1986, vol. 15 (3), pp. 351-362.
Tasker et al., "Metal Complexes For Hydrometallurgy and Extraction," Comprehensive, Coordination Chemistry, Jan. 1, 2003,pp. 759-808.
Final Office Action for U.S. Appl. No. 15/568,230, dated Nov. 18, 2020 (7 pages).
Hageluken., "Improving Resource Recovery From Electronic Scrap Recycling—A Holistic Approach," Umicore Precious Metals Refining. (10 pages).
Advisory Action for U.S. Appl. No. 15/568,230, dated Mar. 8, 2019 (2 pages).
Final Office Action for U.S. Appl. No. 15/568,230, dated Dec. 31, 2018 (12 pages).
Final Office Action for U.S. Appl. No. 15/568,230, dated Nov. 26, 2019 (7 pages).
Non-Final Office Action for U.S. Appl. No. 15/568,230, dated Apr. 30, 2018 (11 pages).
Non-Final Office Action for U.S. Appl. No. 15/568,230, dated May 21, 2019 (8 pages).
Non-Final Office Action for U.S. Appl. No. 15/568,230, dated May 18, 2020 (7 pages).
Office Action for Chinese Patent Application No. 201680036516.9, dated Dec. 29, 2018—English Translation Available (23 pages).
Office Action for Chinese Patent Application No. 201680036516.9, dated Aug. 30, 2019—English Translation Available (23 pages).
Corrected Notice of Allowability for U.S. Appl. No. 15/568,245, dated Jul. 7, 2022 (2 pages).
Corrected Notice of Allowability for U.S. Appl. No. 15/568,230, dated Jul. 7, 2022 (3 pages).
Notice of Allowance for U.S. Appl. No. 15/568,245, dated Mar. 25, 2020 (7 pages).
Notice of Allowance for U.S. Appl. No. 15/568,245, dated Aug. 11, 2020 (10 pages).
Non-Final Office Action for U.S. Appl. No. 15/568,245, dated Oct. 24, 2019 (7 pages).
International Search Report and Written Opinion for International Patent Application No. PCT/CA2016/050459, dated Aug. 26, 2016 (9 pages).
Office Action for Chinese Patent Application No. CN202111186852.0, dated Oct. 21, 2022 (23 pages).
Office Action for Canadian Patent Application No. 2,983,353, dated Nov. 21, 2022 (4 pages).
Office Action for Canadian Patent Application No. 2,983,350, dated Nov. 21, 2022 (4 pages).

(56) References Cited

OTHER PUBLICATIONS

International Preliminary Report on Patentability for International Patent Application No. PCT/CA2021/051102 dated Feb. 7, 2023 (8 pages).
Office Action for Japanese Patent Application No. 2022-094051 dated Mar. 7, 2023 (2 pages).
International Preliminary Report on Patentability for International Patent Application No. PCT/CA2021/051351, dated Mar. 28, 2023 (8 pages).
International Preliminary Report on Patentability for International Patent Application No. PCT/CA2021/051385, dated Mar. 28, 2023 (8 pages).
Office Action for Indian Patent Application No. 201717040510, dated Mar. 31, 2023 (2 pages).
Office Action for Canadian Application No. 2983350 dated Aug. 24, 2023 (3 pages).
Office Action for Canadian Application No. 2,983,353 dated Sep. 22, 2023 (5 pages).

* cited by examiner

METHODS FOR SIMULTANEOUS LEACHING AND EXTRACTION OF PRECIOUS METALS

FIELD

The present application relates to methods for the simultaneous leaching and extraction of precious metals. For example, the present application relates to methods of leaching and extracting gold and/or palladium from a substance comprising gold and/or palladium such as a gold- and/or palladium-containing ore which is optionally done in one step using a compound of the present application.

BACKGROUND

Gold is an element in the periodic table which belongs to the same group as silver and copper. It is usually found in combination with these metals in ores. The average concentration of copper and silver in Earth's crust is 50 and 0.07 ppm (parts per million) respectively while for gold it is just 0.005 ppm[1].

[1] J. Mardsen, I. House, The Chemistry of Gold Extraction. 1992, West Sussex, England.

Ore deposits with a concentration of 0.5 ppm or higher are considered to be economically recoverable. Due to its limited sources, gold recovery not only from ores, but also from secondary sources has become more and more important during the last decades. The annual production of gold from the gold mining industry is more than 2500 tonnes worldwide[2]. In addition, about 900 tonnes of secondary gold is recovered from different sources such as but not limited to anode slime and jewelry, dentistry and electronic scraps[3].

[2] E. B. Amey, "Gold" USGS Mineral Yearbook 2004 (Washington, D.C., USGS, 2004), pp. 34.1-34.9.

[3] Anonymous, "Gold" Mining Journal, (Jun. 11, 2004), pp. 19-24.

The most commonly used process for gold recovery from ore includes the use of highly toxic inorganic cyanides (e.g., NaCN, KCN) to convert gold(0) into a water-soluble $Au(CN)_2^-$ coordination complex by a process known as leaching. An example of a known process 10 for gold recovery using cyanide leaching is shown in FIG. 1. In process 10, low grade ore 12 is crushed and ground 14 then leached 16 with a basic solution of NaCN for 16 to 48 hours depending on ore type. Because of some environmental accidents in various gold mines around the world, gold leaching by cyanidation has been prohibited in many countries[4]. Therefore, considerable efforts have been made to find an alternative to cyanide and a variety of leaching reagents have been studied and proposed[5,6].

[4] A. C. Grosse, G. W. Dicinoski, M. J. Shaw, P. R. Haddad, Hydrometallurgy 2003, 69, 1-21.

[5] I. Chandra, M. I. Jeffrey, Hydrometallurgy 2005, 77, 191-201.

[6] G. A. Munoz, J. D. Miller, Minerals and Metallurgical Processing, 2000, 17, 198-204.

Generally, following gold dissolution in the cyanide solution, gold is recovered by activated carbon adsorption (e.g. step 18 in process 10 of FIG. 1 wherein, for example 0.1 to 1 kg activated carbon per ton ore is used), or by the zinc cementation process. The activated carbon adsorption process is considerably more common[7,8]. For example, 4 to 8 kg gold can be adsorbed by 1 ton activated carbon in 4 to 8 steps over a time period of 4 to 8 hours.

[7] Dai, X., Breuer, P. L., Jeffrey, M. I. Minerals & Metallurgical Processing, 2010, 27, 190-195.

[8] M. D. Adams, B. Sceresini, Elsevier, 2005, 789-824.

As shown in FIG. 1, following the carbon adsorption step 18, the loaded activated carbon is washed 20 with low concentrated HCl to remove impurities such as adsorbed Zn, Ca, Fe, Cu and Ag then gold desorption (elution) 22 is done by using, for example 1% NaOH and 0.1 to 0.2% NaCN solution at a high temperature (e.g. 110° C.) for 36 to 72 hours. Pure gold 24 can be obtained, for example by electrowinning or reduction. The whole process time for gold recovery using a process like the process 10 shown in FIG. 1 is 46-110 hours.

Processes for gold recovery which use activated carbon may suffer from several drawbacks such as but not limited to low selectivity, very long procedures, loss of gold product, high temperature requirements, and further consumption of cyanide for desorption of gold from activated carbon, all of which may bring additional costs during the gold recovery process[9].

[9] J. Z. Jiang, W. J. Zhou, H. C. Gao, J. G. Wu, G. X. Xu, and J. Chen. J. Inorg. Chem. 2001, 17, 343-48.

Although considerable effort has been undertaken to replace cyanide, none of the reported leaching reagents has been used in the industrialization of gold production due, for example to drawbacks such as (i) high reagent consumption, (ii) complex chemistry, (iii) lack of industrial techniques for the recovery of gold from their resulting solutions, and (iv) low rate of gold recovery compared to cyanide. Drawbacks such as toxicity, cost, long reaction times and poor selectivity are also associated with known systems. Thus, it may be desirable to develop more effective leachants with, for example, higher efficiency and/or lower toxicity from both an environmental and an economical viewpoint.

Cyanide Leaching

For more than a century, cyanidation has remained the dominant process for extraction and recovery of gold from ore. Metallic gold can be dissolved in an alkaline solution of potassium or sodium cyanide in the presence of dissolved molecular oxygen (reaction 1):

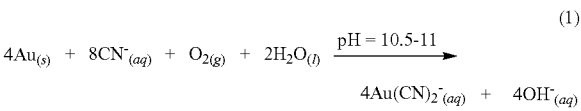

$$4Au_{(s)} + 8CN^-_{(aq)} + O_{2(g)} + 2H_2O_{(l)} \xrightarrow{pH = 10.5-11} 4Au(CN)_2^-{}_{(aq)} + 4OH^-_{(aq)} \quad (1)$$

In neutral or acidic conditions, over 99% of the cyanide will exist as highly poisonous HCN gas. By increasing pH, it is converted to free cyanide ion so that at a pH of 9.3, $CN^-$ and HCN are in equilibrium, with 50% of each present. At a pH of 11, over 99% of the cyanide remains in solution as $CN^-$.[10] The free cyanide ion is a very strong ligand which can form a highly stable complex with gold, $Au(CN)_2^-$, in aqueous solution. With stoichiometric ratios, gold dissolution in alkaline cyanide solution is slow, but by increasing the cyanide concentration, the leaching rate will increase until a maximum is reached (0.075 w/w % KCN or 0.06% NaCN) and after that the rate of dissolution remains constant[11].

[10] P. D. Kondos, G. Deschénes, R. M. Morrison, Hydrometallurgy, 1995, 39, 235-250.

[11] F. Habashi, A Textbook of Hydrometallurgy, Métallurgie Extractive Québec, Québec City, Canada, second edition, 1999.

Before cyanide treatment, the gold ore is typically crushed and ground to decrease the size of the ore particles to 75 microns or less to provide a larger contact surface area between the gold and the leaching solution. Depending on the ore type, the cyanide consumption varies from about 0.25 to 2 kg of cyanide per tonne of ore and the rate of gold dissolution in cyanide takes 16 to 48 hours[11]. The cyanide consumption increases when the refractoriness of the gold ore is increased. A refractory gold ore is a gold-containing ore that is resistant to recovery by direct cyanidation. Other minerals and metals are also dissolved in the alkaline cyanide solution and they usually consume cyanide and oxygen and thus reduce the overall efficiency of gold leaching.

[11] F. Habashi, *A Textbook of Hydrometallurgy*, Métallurgie Extractive Québec, Québec City, Canada, second edition, 1999.

For example, copper minerals such as chalcocite ($Cu_2S$) and cuprite ($Cu_2O$) can form a variety of cyanide complexes such as CuCN, $Cu(CN)_2^-$, $Cu(CN)_3^{2-}$ and $Cu(CN)_4^{3-}$ and iron sulfides like pyrrhotite ($Fe_7S_8$), pyrite ($FeS_2$) and arsenopyrite (FeAsS) form highly stable $Fe(CN)_6^{4-}$ and $Fe(CN)_6^{3-}$ complexes[12]. In addition, most sulfide minerals have a detrimental effect on gold leaching since they may passivate the surface of gold and consume cyanide and oxygen. However, some other minerals such as galena (PbS) can improve gold leaching kinetics by preventing formation of a passivation layer on the gold surface[13].

[12] G. Q. Lui, W. T. Yen, *Minerals Engineering*, 1995, 8, 111-123.
[13] G. Deschênes, G. Wallingford, *Minerals Engineering*, 1995, 8, 923-931.

Although cyanide is still the main leaching reagent for gold recovery in the mining industry, it suffers from several drawbacks such as but not limited to high toxicity, slow leaching kinetics and low gold extraction for refractory ores. Considerable efforts have thus been made to find an alternative to cyanide.

Gold Recovery from Cyanide Solution

There are several techniques for gold recovery from cyanide leach liquors like carbon adsorption, zinc cementation and solvent extraction with carbon adsorption being by far the more common technique[14,15]. In the carbon adsorption technique, after gold is leached into cyanide solution, activated carbon is applied for selective gold adsorption to separate $AuCN_2^-$ from other metals and impurities. 0.1 to 1 kg activated carbon per tonne of ore is usually applied in 4 to 8 steps for complete adsorption of $Au(CN)_2^-$ complex from cyanide solution which takes 4 to 8 hours. The loaded activated carbon is usually washed with a low concentration HCl solution to remove other impurities such as Fe, Cu, Zn, Ca, and Ag. The dicyanoaurate(I) complex is then removed from the activated carbon in an elution step by washing the loaded activated carbon with a fresh basic sodium cyanide solution at 110° C. for 36 to 72 hours[10,16]. The desorbed $Au(CN)_2^-$ complex is finally reduced to elemental gold by electrowinning or reduction.

[14] Grosse, A. C.; Dicinoski, G. W.; Shaw, M. J.; Haddad, P. R. *Hydrometallurgy*, 2003, 69, 1-21.
[15] Dai, X., Breuer, P. L., Jeffrey, M. I. *Minerals & Metallurgical Processing*, 2010, 27, 190-195.
[10] P. D. Kondos, G. Deschênes, R. M. Morrison, *Hydrometallurgy*, 1995, 39, 235-250.
[16] Grosse, A. C. Dicinoski, G. W. Shaw, M. J. Haddad, P. R. *Hydrometallurgy*, 2003, 69, 1-21.

The activated carbon method suffers from several drawbacks such as but not limited to low selectivity, very long procedures, loss of some gold product, and high temperature requirements[17].

[17] J. Z. Jiang, W. J. Zhou, N. C. Gao, J. G. Wu, G. X. Xu, and J. Chen. *J. Inorg. Chem.* 2001, 17,343-48.

Alternatives to Cyanide

Due to the high toxicity and environmental problems of cyanide, there has been a quest to find useful alternatives. In recent years, some alternatives to cyanide have been reported to leach gold ore efficiently. Some of the useful reported leaching reagents are thiosulfate, thiocyanite, thiourea, and chloride in combination with an oxidizing agent like $HNO_3$, $H_2O_2$ and hypochlorite.

Thiosulfate Leaching

Thiosulfate is the most studied alternative to cyanide. Gold can be leached in alkaline aqueous solutions (pH=9.5-10.5) of thiosulfate in the presence of oxidizing agents like $O_2$ and copper(II) ions. The rate of gold dissolution becomes slower in the absence of copper (II) ions[18]. Ammonia is usually used to accelerate the rate of gold leaching in this media. It has an efficient role to stabilize the intermediate oxidation products of gold, decreasing the rate of thiosulfate oxidation by $Cu^{2+}$, preventing the formation of insoluble components like sulfides on the gold surface and keeping a high concentration of $Cu^{2+}$ by forming $Cu(NH_3)_4^{2+}$ during the leaching process[19,20]. Oxygen has a dual role by oxidation of $Cu(NH_3)_2^+$ to $Cu(NH_3)_4^{2+}$ or direct oxidation of the gold surface. The overall balanced equation of gold dissolution in thiosulfate media is shown in the following reaction[21] (2):

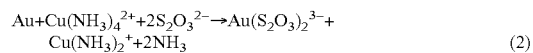

$$Au+Cu(NH_3)_4^{2+}+2S_2O_3^{2-} \rightarrow Au(S_2O_3)_2^{3-}+Cu(NH_3)_2^++2NH_3 \quad (2)$$

[18] X. M. Zhang, G. Senanayake, M. J. Nicol, *Hydrometallurgy*, 2004, 74,243.
[19] G. Rabai, I. R. Epstein, *Inorg. Chem.* 1992, 31, 3239.
[20] S. Zhang, M. J. Nicol, *J Appl. Electrochem*, 2003, 33, 767.
[21] Ritchie, I. M., Nicol, M. J., Staunton, W. P., Young, C. (Ed.), *Cyanide: Social and Economic Aspects*. TMS, Warrendale, 2001, pp. 427-440.

Compared to the cyanidation process, thiosulfate leaching has some advantages such as but not limited to fast leaching kinetics, lower toxicity and higher gold recovery in the case of some refractory gold ores[22,23]. However, it suffers from some major drawbacks such as but not limited to complex chemistry, toxicity of ammonia, ineffectiveness of activated carbon for desorption of leached gold, and high consumption of thiosulfate.

For example, the copper(II) itself consumes thiosulfate resulting in high consumption of both thiosulfate and copper and the resulting tetrathionate ($S_4O_6^{2-}$) decomposes to elemental sulfur and forms sulfides such as CuS which increases the gold passivation during the leaching process (reaction 3)[24,25].

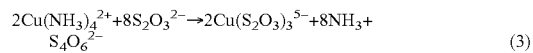

$$2Cu(NH_3)_4^{2+}+8S_2O_3^{2-} \rightarrow 2Cu(S_2O_3)_3^{5-}+8NH_3+S_4O_6^{2-} \quad (3)$$

[22] Berezowsky, R. M. G. S., Sefton, V. B., 108th *AIME Annual Meeting*, New Orleans, La., 1979, pp. 1-17.
[23] Aylmore, M. G., Muir, D. M, *Miner. Eng.* 2001, 14,135-174.
[24] Breuer, P. L., Jeffrey, M. I., *Hydrometallurgy*, 2003, 70,163-173.
[25] Feng, D., van Deventer, J. S. J., *Hydrometallurgy*, 2006, 82,126-132.

Thiourea

Thiourea is another well-studied leaching reagent which can dissolve gold in acidic media based on the following reaction (4)[26]:

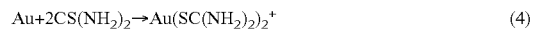

$$Au+2CS(NH_2)_2 \rightarrow Au(SC(NH_2)_2)_2^+ \quad (4)$$

[26] Kazakov, V. P.; Lapshin, A. I.; Peshchevitskii, B. I. Russ. *J. Inorg. Chem.* 1964, 9,708.

Different oxidizing reagents such as but not limited to hydrogen peroxide, sodium peroxide, oxygen, ozone and ferric ion can be used in combination with thiourea to dissolve gold. Among these oxidizing reagents, ferric ion in sulfuric acid solution is a useful one (reaction 5)[27].

$$Au+2CS(NH_2)_2+Fe^{3+} \rightarrow Au(SC(NH_2)_2)_2^++Fe^{2+} \quad (5)$$

[27] Plaskin, I. N. and Kozhukhova, M. A, *Sbornik Nauchnykh Trudov, Institut Tsvetnykh Metallov*, 1960, 33,107-119.

However, thiourea is not stable in acidic media in the presence of ferric ion and is decomposed to sulfur and cyanamide[28]. Addition of a reducing agent such as $SO_2$ decreases the thiourea consumption by preventing its oxidation[29]. The kinetics of gold leaching in thiourea solution are much faster than the cyanidation process because of nongaseous oxidants such as but not limited to hydrogen peroxide and ferric sulfate which are used instead of oxygen which is used in the cyanidation process[30]. However, gold recovery and reagent consumption with cyanide is more economical than thiourea[31].

[28] Preisler, P. W. and Berger, L., *Journal of the American Chemical Society*, 1947, 69,322-325.
[29] Schulze, R. G., 1984, *Journal of Metals*, 1984, 36,62-65.
[30] Groenewald, T., *Hydrometallurgy*, 1976, 1, 277-290.
[31] Gönen, N., *Hydrometallurgy*, 2003, 69,169-176.

Complexation with base metals such as copper accelerates thiourea consumption and decreases gold leaching kinetics. Thermal degradation, oxidation by the ferric sulfate and air are the other reasons for high consumption of thiourea[32]. Thiourea's commercial application has been hindered due to its high consumption and no existence of applicable industrial techniques for the recovery of gold from its solution. Although thiourea has a lower toxicity compared to cyanide, it is suspected to be a carcinogen agent and is treated with caution[33].

[32] Krzewska, S. and Podsiadly, H., *Journal of Inorganic and Nuclear Chemistry*, 1980, 42,83-86.
[33] Örgül, S., Atalay, Ü. *Hydrometallurgy*, 2002, 67,71-77.

Chloride Solution Containing an Oxidizing Agent

Concentrated hydrochloric acid in combination with powerful oxidizing agents is known as a strong leaching reagent for leaching precious metals, for example from scraps and secondary sources[34]. A hot solution of concentrated HCl mixed with concentrated $HNO_3$ (known as aqua regia) or hydrogen peroxide can dissolve gold according to the following chemical reactions (see reactions 6 and 7) resulting in the formation of a stable $AuCl_4^-$ complex[35].

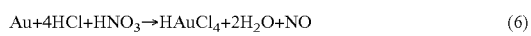

$$Au + 4HCl + HNO_3 \rightarrow HAuCl_4 + 2H_2O + NO \quad (6)$$

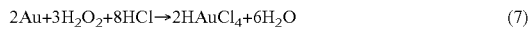

$$2Au + 3H_2O_2 + 8HCl \rightarrow 2HAuCl_4 + 6H_2O \quad (7)$$

[34] J. W. Mellor, *A Comprehensive Treatise of Inorganic and Theoretical Chemistry* (London: Longman Green & Co., 1923), p. 499.
[35] F. Habashi, *Principles of Extractive Metallurgy*, Vol. 2$^{nd}$ ed. (New York: Gordon and Breach, 1980), p. 39.

Apart from these oxidants, chlorine gas can also be used which forms the same gold species[36]. Chlorine had been used to dissolve gold from ores and concentrates during the second half of the 19$^{th}$ century until it was gradually replaced by the more economical alkaline cyanide leaching. In all cases, the dissolution rate is faster compared to cyanide, however, due to high concentration of HCl, all of these solutions are highly corrosive and toxic and in the case of gold ore treatment, their consumption is not economical[37].

[36] Finkelstein, N. P., Hoare, R. M., James, G. S., Howat, D. D., *Journal of the South African Institute of Mining and Metallurgy*, 1996, 67, 196-215.
[37] Filmer, A. O., Lawrence, P. R., Hoffman, W., 1984. *A comparison of cyanide, thiourea, and chlorine as lixiviants for gold*. Gold-Mining, Metallurgy, and Geology. Australasian Institute of Mining and Metallurgy, Melbourne, pp. 279-287.

Chloride/Hypochlorite

Chloride/hypochlorite solutions have been recognized as another alternative leaching reagent to cyanide which can dissolve gold in a wide range of pH values[38]. Depending on the solution's pH, three different oxidizing species can be formed in hypochlorite solutions. At pH >7.5, hypochlorite ion (OCl$^-$) is the dominant species while for pH values between 3.5 and 7.5, hypochlorous acid (HOCl) acts as oxidizing agent and for pH less than 3.5, nascent chlorine gas ($Cl_2$) is formed. Among these three species, HOCl is the most effective oxidizing agent to leach gold as the $[AuCl_4]^-$ (reaction 8)[39].

$$2Au + 3HOCl + 3H^+ + 5Cl^- \rightarrow 2[AuCl_4]^- + 3H_2O \quad (8)$$

[38] Ikiz, D., Gulfen, M., Aydin, A. O. *Minerals Engineering*, 2006, 19, 972-974.
[39] Jeffrey, M. I., Breuer, P. L., Choo, W. L. *Metall. Mater. Trans.* 2001, B 32, 979-986.

In a solution containing 100 g/L NaCl, the $[AuCl_4]^-$ is stable in the pH range of 0-8 and potentials greater than 0.9 V[40]. The chloride-hypochlorite solution is a useful leaching reagent, for example for refractory gold ores. Because of low acidity, it does not produce a corrosion media; however the reagents consumption is still high[41,42]. The main drawback of this leaching reagent is that the percentage of leached gold is usually less than 85%[43].

[40] Nesbitt, C. C., Milosavljevic, E. B., Hendrix, J. L., *Chem. Res.* 1990, 29, 1696-1700.
[41] Ghobeiti Hasab, M., Rashchi, F., Raygan, Sh. *Miner. Eng.* 2013, 50-51, 140-142.
[42] Ghobeiti Hasab, M., Raygan, Sh., Rashchi, F., *Hydrometallurgy*, 2013, 138, 59-64.
[43] Cheng, Y. Shen, S. Zhang, J. Chen, S. Xiong, L. Liu J. *Ind. Eng. Chem. Res.* 2013, 52, 16622-16629.

SUMMARY

The methods of the present application are directed to eliminating the use of both cyanide (which is highly toxic) and activated carbon (which is one of the most expensive steps in known processes) for the selective recovery of precious metals such as gold, for example, in the mining industry. For example, the sulfur-based ligand extractant(s) of the present application can be used in a simultaneous leaching and solvent extraction system to accelerate the leaching process over known processes. Extractants with higher selectivities are useful in light of environmental and/or economic concerns. No solvent extraction system has ever been implemented in the industrialization of gold production. The methods of the present application can, for example, shorten the entire gold processing time to hours at room temperature with high selectivity and minimal amounts of acid and oxidants, while the current gold recovery process takes 2-3 days, employs highly toxic cyanide and uses temperatures of up to 110 degrees Celsius in some steps of the process.

The methods of the present application can be implemented into current industrial processes such as gold extraction processes with minimal financial costs and effort. The entire cost of gold recovery by the cyanidation process is at least $10,000 per kg of gold of which the cost of gold recovery by the activated carbon step represents circa 25% of the overall cost (i.e. $2500 per kg gold). However, the cost of activated carbon is not the only issue; the majority of the expense is in the time required in the extraction step as well as the use of elevated temperatures. The activated carbon extraction step is a lengthy process using 36-72 hours at 110° C. The present methods eliminate the use of cyanide and activated carbon using highly selective ligands that presently cost, for example, $7-12/kg and in doing so, decreases overall gold recovery times while maintaining high extraction efficiencies. An environmental benefit arises from the elimination of sodium cyanide in the gold mining process. Other advantages may include, for example, greater simplicity, lower costs, considerably shorter extraction times at room temperature and the provision of a cleaner, safer and more environmentally friendly alternative to the existing cyanide process.

Accordingly, the present application includes a method of leaching and extracting gold and/or palladium from a substance comprising gold and/or palladium, the method comprising:

treating a mixture comprising an aqueous phase comprising an acid, an oxidizing agent and the substance, and an organic phase comprising a water-immiscible organic solvent and a compound of Formula I:

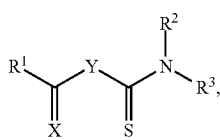

I wherein
$R^1$ is —$NR^4R^5$ or aryl;
$R^2$ and $R^3$ are each independently selected from H, $C_{1-10}$ alkyl, $C_{3-10}$ cycloalkyl, $C_{1-6}$ alkylene $C_{3-10}$ cycloalkyl, heterocycloalkyl and aryl; or
$R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$ alkyl;
$R^4$ and $R^5$ are each independently selected from H, $C_{1-10}$ alkyl, $C_{3-10}$ cycloalkyl, $C_{1-6}$ alkylene $C_{3-10}$ cycloalkyl, heterocycloalkyl and aryl; or
$R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$ alkyl;
X is O or S;
Y is S, $NR^6$ or $CR^6R^7$; and
$R^6$ and $R^7$ are each independently selected from H, $C_{1-10}$ alkyl, $C_{3-10}$ cycloalkyl, $C_{1-6}$ alkylene $C_{3-10}$ cycloalkyl, heterocycloalkyl and aryl, under conditions to leach the gold and/or palladium from the substance and extract the gold and/or palladium by forming a complex between the leached gold and/or palladium and the compound of Formula I, in one step.

In an embodiment, the compound of Formula I is a compound of Formula I(a):

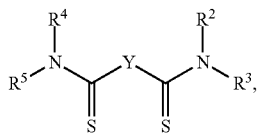

I(a)

wherein $R^2$, $R^3$, $R^4$, $R^5$ and Y are as defined for the compound of Formula I.

In an embodiment, for example, in the compound of Formula I(a), only one of $R^2$, $R^3$, $R^4$ and $R^5$ is H.

In an embodiment, for example, in the compound of Formula I(a), $R^2$ and $R^3$ together with the nitrogen atom to which they are attached form a heterocycloalkyl or a substituted heterocycloalkyl, wherein the heterocycloalkyl is selected from aziridinyl, azetidinyl, pyrrolidinyl, piperidinyl, azepanyl, azocanyl, imidazolidinyl, oxazolidinyl, thiazolidinyl, piperazinyl, hexahydropyrimidinyl, morpholinyl, 1,3-oxazinanyl, thiomorpholinyl, 1,3-thiazinanyl, 1,3-diazepanyl, 1,3-oxazepanyl, 1,3-thiazepanyl, 1,4-diazepanyl, 1,4-oxazepanyl, 1,4-thiazepanyl, 1,3-diazocanyl, 1,3-oxazocanyl, 1,3-thiazocanyl, 1,4-diazocanyl, 1,4-oxazocanyl, 1,4-thiazocanyl, 1,5-diazocanyl, 1,5-oxazocanyl and 1,5-thiazocanyl.

In another embodiment, for example, in the compound of Formula I(a), $R^2$ and $R^3$ together with the nitrogen atom to which they are attached form morpholinyl, pyrrolidinyl or 4-methylpiperidinyl.

In an embodiment, for example, in the compound of Formula I(a), $R^4$ is H and $R^5$ is $C_{1-6}$ alkyl or $C_{3-8}$ cycloalkyl.

In an embodiment, Y is $NR^6$.

In an embodiment, $R^6$ is H, $C_{1-6}$ alkyl or $C_{3-8}$ cycloalkyl.

In an embodiment, the compound of Formula I is a compound of Formula I(a)(i), I(a)(ii), I(a)(iii) or I(a)(iv):

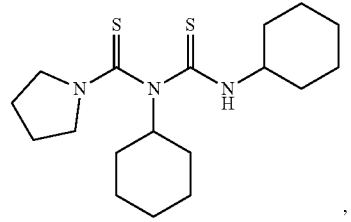

I(a)(i)

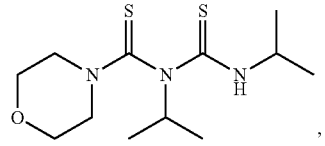

I(a)(ii)

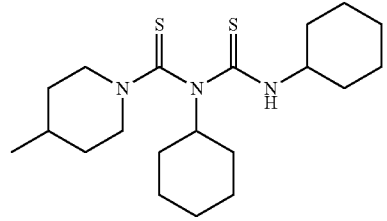

I(a)(iii)

or

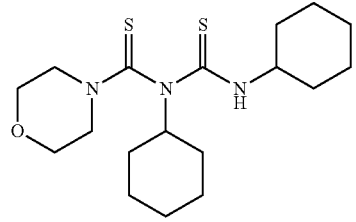

I(a)(iv)

In another embodiment of the present application, the compound of Formula I is the compound of Formula I(a)(i):

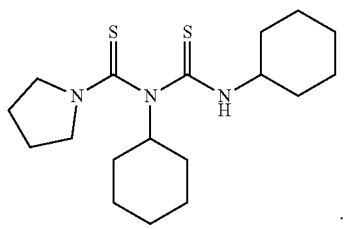

I(a)(i)

In another embodiment of the present application, the compound of Formula I is the compound of Formula I(b)(i):

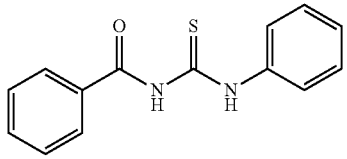

I(b)(i)

In an embodiment, the molar ratio of the compound of Formula I to the gold and/or palladium is about 3:1 to about 4:1.

In another embodiment, the acid is HCl having a concentration in the aqueous solution of about 1 M to about 2 M. In a further embodiment, the oxidizing agent is $HNO_3$ having a concentration in the aqueous solution of about 0.1 M to 1.0 M. It is an embodiment that the water-immiscible organic solvent is selected from dichloromethane, chloroform and chlorobenzene.

In an embodiment, the conditions to leach the gold and/or palladium from the substance and extract the gold and/or palladium by forming a complex between the leached gold and/or palladium and the compound of Formula I in one step comprise stirring the mixture for a time of about 2 hours to about 10 hours at a temperature of about 10° C. to about 40° C.

In an embodiment, the method further comprises separating the mixture into an aqueous phase and an organic phase comprising the complex between the leached gold and/or palladium and the compound of Formula I.

In an embodiment, the method further comprises stripping the gold and/or palladium from the complex between the compound of Formula I and the gold and/or palladium by a method comprising contacting the organic phase with an aqueous solution comprising an acid and thiourea under conditions to obtain a gold and/or palladium-containing strip solution and a gold and/or palladium-reduced organic phase comprising the compound of Formula I.

In another embodiment, the method further comprises separating the gold and/or palladium-containing strip solution from the gold and/or palladium-reduced organic phase comprising the compound of Formula I and recovering gold and/or palladium from the gold and/or palladium-containing strip solution by electrowinning or reduction.

In a further embodiment of the present application, the method further comprises recycling the compound of Formula I from the gold and/or palladium-reduced organic phase, for example, for use in the step of contacting a gold and/or palladium-containing substance with the mixture.

In an embodiment, the method further comprises recovering gold and/or palladium from the organic phase by direct reduction.

In an embodiment, the substance comprising gold and/or palladium is a gold-containing substance. In another embodiment of the present application, the gold-containing substance is a gold-containing ore.

The present application also includes a use of a compound of Formula I:

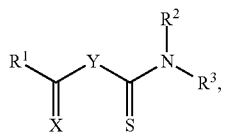

I wherein
$R^1$ is —$NR^4R^5$ or aryl;
$R^2$ and $R^3$ are each independently selected from H, $C_{1-10}$ alkyl, $C_{3-10}$ cycloalkyl, $C_{1-6}$ alkylene $C_{3-10}$ cycloalkyl, heterocycloalkyl and aryl; or
$R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$ alkyl;
$R^4$ and $R^5$ are each independently selected from H, $C_{1-10}$ alkyl, $C_{3-10}$ cycloalkyl, $C_{1-6}$ alkylene $C_{3-10}$ cycloalkyl, heterocycloalkyl and aryl; or
$R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$ alkyl;
X is O or S;
Y is S, $NR^6$ or $CR^6R^7$; and
$R^6$ and $R^7$ are each independently selected from H, $C_{1-10}$ alkyl, $C_{3-10}$ cycloalkyl, $C_{1-6}$ alkylene $C_{3-10}$ cycloalkyl, heterocycloalkyl and aryl, for leaching and extracting gold and/or palladium in one step from a substance comprising gold and/or palladium.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The present application will now be described in greater detail with reference to the drawings in which.

DETAILED DESCRIPTION

I. Definitions

Figure 1:
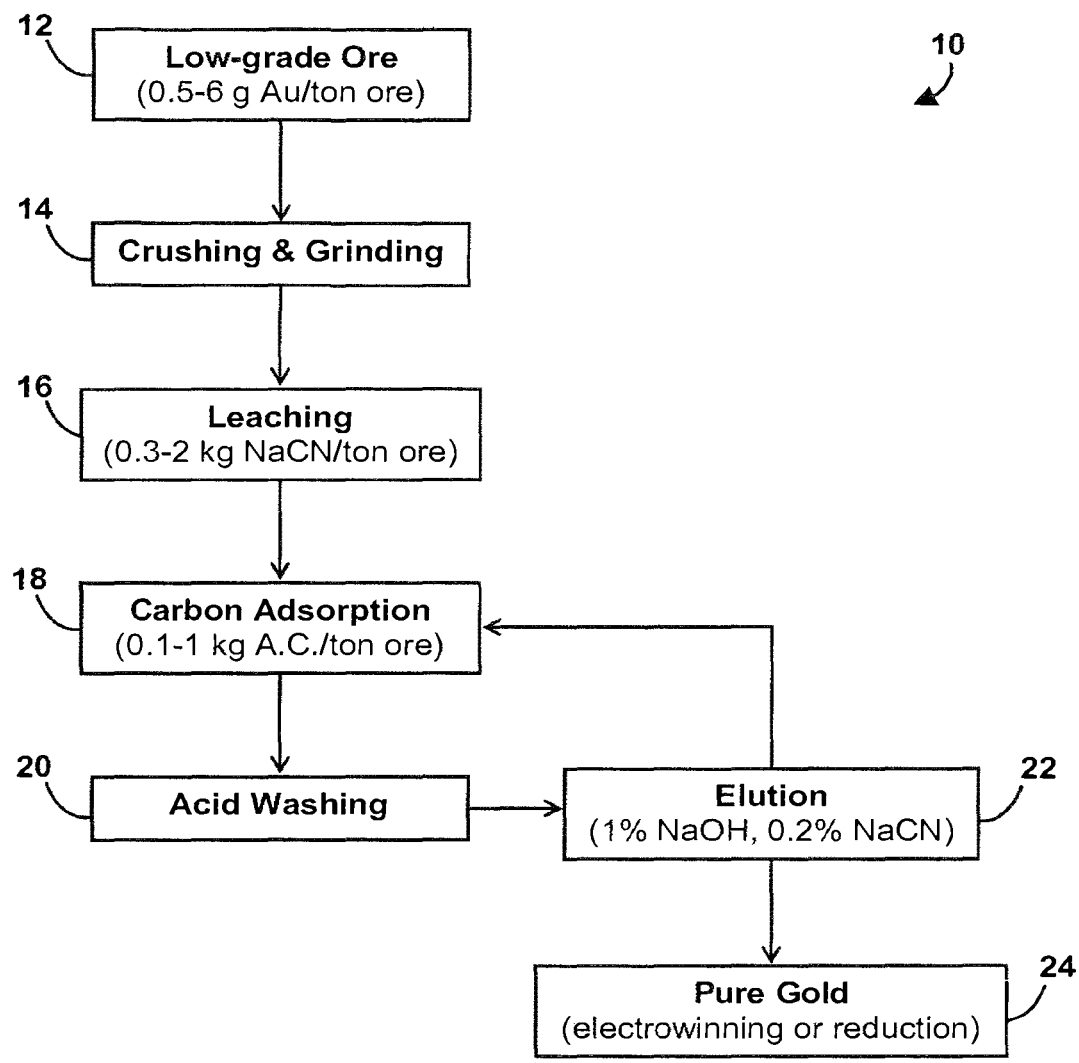
FIG. 1 shows a schematic representation of a process of gold recovery using cyanide leaching according to the prior art.

Unless otherwise indicated, the definitions and embodiments described in this and other sections are intended to be applicable to all embodiments and aspects of the present application herein described for which they are suitable as would be understood by a person skilled in the art.

The term "compound of the present application" and the like as used herein refers to a compound of Formula I as defined herein.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In embodiments of the present application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

The term "suitable" as used herein means that the selection of specific reagents or conditions will depend on the reaction being performed and the desired results, but nonetheless, can generally be made by a person skilled in the art once all relevant information is known.

The term "immiscible" as used herein when referring to two liquid phases means that the two liquid phases cannot be mixed to form a solution having a single phase under the conditions used, such as the relative proportions of the two liquid phases and/or the temperature, etc. Two immiscible liquid phases will, for example separate into two liquid phases after mixing. Each of these two liquid phases may, for example contain small amounts of the other liquid phase. Accordingly, a "water-immiscible" liquid such as a "water-immiscible organic solvent" is a liquid that cannot be mixed with water to form a solution having a single phase under the conditions used but that may, for example contain small amounts of water after being mixed with water.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-10}$ alkyl means an alkyl group having 1, 2, 3, 4, 5, 6, 7, 8, 9 or 10 carbon atoms.

The term "alkylene" as used herein, whether it is used alone or as part of another group, means straight or branched chain, saturated alkylene group, that is, a saturated carbon chain that contains substituents on two of its ends. The number of carbon atoms that are possible in the referenced alkylene group are indicated by the numerical prefix "$C_{n1-n2}$". For example, the term $C_{1-6}$ alkylene means an alkylene group having 1, 2, 3, 4, 5 or 6 carbon atoms.

The term "cycloalkyl," as used herein, whether it is used alone or as part of another group, means saturated alkyl groups having at least one cyclic ring. The number of carbon atoms that are possible in the referenced cycloalkyl group are indicated by the numerical prefix "$C_{n1-n2}$". For example, the term $C_{3-10}$ cycloalkyl means a cycloalkyl group having 3, 4, 5, 6, 7, 8, 9 or 10 carbon atoms.

The term "heterocycloalkyl" as used herein, whether it is used alone or as part of another group, refers to a non-aromatic, ring-containing group having one or more multivalent heteroatoms, independently selected from N, O and S, as a part of the ring structure and including at least 3 and up to 20 atoms in the ring(s). Heterocycloalkyl groups are either saturated or unsaturated (i.e. contain one or more double bonds) and may contain more than one ring.

The term "aryl" as used herein, whether it is used alone or as part of another group, refers to cyclic groups that contain at least one aromatic ring. In an embodiment of the application, the aryl group contains from 6, 9, 10 or 14 atoms, such as phenyl, naphthyl, indanyl or anthracenyl.

The term "heteroaryl" as used herein, whether it is used alone or as part of another group, refers to an aromatic, ring-containing group having one or more multivalent heteroatoms, independently selected from N, 0 and S, as a part of the ring structure and including at least 5 and up to 20 atoms in the ring(s). Heteroaryl groups may contain more than one ring.

II. Methods and Uses of the Application

In the methods of the present application, both leaching and extraction of metal steps are done simultaneously which can increase the overall efficiencies of the process over known methods for leaching and extracting metals such as gold in which these steps are conducted separately. Using the methods of the present application, greater than 99.9% gold recovery has been achieved with gold powder in only four hours using very low concentrations of acid (1 M HCl) at room temperatures. Increasing HCl concentration to 2 M reduced gold recovery times to two hours. To investigate the selectivity of the methods of the present application, a mixture of different metals was treated. The method was found to be highly selective for gold in the presence of large amounts of transition metal impurities such as Fe, Cu, Zn and Ag. Compared to known methods, on top of eliminating the need for cyanide and activated carbon, the methods of the present application also can eliminate the need for an acid washing step to remove impurities.

Accordingly, the present application includes a method of leaching and extracting gold and/or palladium from a substance comprising gold and/or palladium, the method comprising:

treating a mixture comprising an aqueous phase comprising an acid, an oxidizing agent and the substance, and an organic phase comprising a water-immiscible organic solvent and a compound of Formula I:

I wherein $R^1$ is —$NR^4R^5$ or aryl;

$R^2$ and $R^3$ are each independently selected from H, $C_{1-10}$ alkyl, $C_{3-10}$ cycloalkyl, $C_{1-6}$ alkylene $C_{3-10}$ cycloalkyl, heterocycloalkyl and aryl; or $R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$alkyl;

$R^4$ and $R^5$ are each independently selected from H, $C_{1-10}$ alkyl, $C_{3-10}$ cycloalkyl, $C_{1-6}$ alkylene $C_{3-10}$ cycloalkyl, heterocycloalkyl and aryl; or $R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$ alkyl;

X is O or S;

Y is S, $NR^6$ or $CR^6R^7$; and $R^6$ and $R^7$ are each independently selected from H, $C_{1-10}$ alkyl, $C_{3-10}$ cycloalkyl, $C_{1-6}$ alkylene $C_{3-10}$ cycloalkyl, heterocycloalkyl and aryl, under conditions to leach the gold and/or palladium from the substance and extract the gold and/or palladium by forming a complex between the leached gold and/or palladium and the compound of Formula I, in one step.

In an embodiment, $R^1$ is —$NR^4R^5$.

In an alternative embodiment, $R^1$ is aryl. In another embodiment, $R^1$ is $C_{6-10}$ aryl. In a further embodiment, $R^1$ is phenyl.

In another embodiment, the compound of Formula I is a compound of Formula I(a):

I(a)

wherein $R^2$, $R^3$, $R^4$, $R^5$ and Y are as defined for the compound of Formula I.

In an embodiment of the present application, for example, in the compound of Formula I(a), only one of $R^2$, $R^3$, $R^4$ and $R^5$ is H.

In another embodiment of the present application, for example, in the compound of Formula I(a), $R^2$ and $R^3$ together with the nitrogen atom to which they are attached, form a heterocycloalkyl or a heteroaryl, or a substituted heterocycloalkyl or a substituted heteroaryl.

In an embodiment, for example, in the compound of Formula I(a), $R^2$ and $R^3$ together with the nitrogen atom to which they are attached form a heterocycloalkyl or a substituted heterocycloalkyl. In another embodiment, for example, in the compound of Formula I(a), $R^2$ and $R^3$ together with the nitrogen atom to which they are attached form a heterocycloalkyl or a substituted heterocycloalkyl, wherein the heterocycloalkyl is selected from aziridinyl, azetidinyl, pyrrolidinyl, piperidinyl, azepanyl, azocanyl, imidazolidinyl, oxazolidinyl, thiazolidinyl, piperazinyl, hexahydropyrimidinyl, morpholinyl, 1,3-oxazinanyl, thiomorpholinyl, 1,3-thiazinanyl, 1,3-diazepanyl, 1,3-oxazepanyl, 1,3-thiazepanyl, 1,4-diazepanyl, 1,4-oxazepanyl, 1,4-thiazepanyl, 1,3-diazocanyl, 1,3-oxazocanyl, 1,3-thiazocanyl, 1,4-diazocanyl, 1,4-oxazocanyl, 1,4-thiazocanyl, 1,5-diazocanyl, 1,5-oxazocanyl and 1,5-thiazocanyl. In a further embodiment, for example, in the compound of Formula I(a), $R^2$ and $R^3$ together with the nitrogen atom to which they are attached form morpholinyl, pyrrolidinyl or 4-methylpiperidinyl. In an embodiment, for example, in the compound of Formula I(a), $R^2$ and $R^3$ together with the nitrogen atom to which they are attached form morpholinyl. In another embodiment, for example, in the compound of Formula I(a), $R^2$ and $R^3$ together with the nitrogen atom to which they are attached form pyrrolidinyl. In a further embodiment, for example, in the compound of Formula I(a), $R^2$ and $R^3$ together with the nitrogen atom to which they are attached form 4-methylpiperidinyl.

In an embodiment, for example, in the compound of Formula I(a), $R^2$ and $R^3$ together with the nitrogen atom to which they are attached form a heteroaryl or a substituted heteroaryl. In another embodiment of the present application, for example, in the compound of Formula I(a), $R^2$ and $R^3$ together with the nitrogen atom to which they are attached form a heteroaryl. In a further embodiment, for example, in the compound of Formula I(a), $R^2$ and $R^3$ together with the nitrogen atom to which they are attached form a heteroaryl selected from pyrrolyl, imidazolyl, pyrazolyl, oxazolyl, isoxazolyl, thiazolyl, isothiazolyl, 1,2,3-triazolyl, 1,2,4-triazolyl, furazanyl, pyridinyl, pyrazinyl, pyrimidinyl, pyridazinyl, 1,2,3-triazinyl, 1,2,4-triazinyl and 1,3,5-triazinyl.

In an embodiment, for example, in the compound of Formula I(a), $R^4$ is selected from H, $C_{1-10}$ alkyl, $C_{3-10}$ cycloalkyl, $C_{1-6}$ alkylene $C_{3-10}$ cycloalkyl, heterocycloalkyl and aryl. In another embodiment, for example, in the compound of Formula I(a), $R^4$ is selected from H, $C_{1-6}$ alkyl, $C_{3-8}$ cycloalkyl, $C_{1-4}$ alkylene $C_{3-8}$ cycloalkyl, heterocycloalkyl and phenyl. In a further embodiment, for example, in the compound of Formula I(a), $R^4$ is selected from H, $C_{1-6}$ alkyl and $C_{3-8}$ cycloalkyl. It is an embodiment that, for example, in the compound of Formula I(a), $R^4$ is selected from H and $C_{1-4}$ alkyl. In another embodiment of the present application, for example, in the compound of Formula I(a), $R^4$ is H.

In an embodiment, for example, in the compound of Formula I(a), $R^5$ is selected from H, $C_{1-10}$ alkyl, $C_{3-10}$ cycloalkyl, $C_{1-6}$ alkylene $C_{3-10}$ cycloalkyl, heterocycloalkyl and aryl. In another embodiment, for example, in the compound of Formula I(a), $R^5$ is selected from $C_{3-10}$ alkyl, $C_{3-8}$ cycloalkyl, $C_{1-4}$ alkylene $C_{3-8}$ cycloalkyl, heterocycloalkyl and phenyl. In a further embodiment, for example, in the compound of Formula I(a), $R^5$ is selected from $C_{1-6}$ alkyl and $C_{3-8}$ cycloalkyl. It is an embodiment, for example, in the compound of Formula I(a), that $R^5$ is isopropyl or cyclohexyl. In another embodiment, for example, in the compound of Formula I(a), $R^5$ is isopropyl. In a further embodiment, for example, in the compound of Formula I(a), $R^5$ is cyclohexyl.

In an embodiment, at least one of any one of $R^1$ to $R^7$ is aryl. In another embodiment, at least one of any one of $R^1$ to $R^7$ is phenyl.

In an embodiment, for example, in the compound of Formula I(a), $R^4$ is H or $C_{1-4}$ alkyl and $R^5$ is $C_{1-6}$ alkyl or $C_{3-8}$ cycloalkyl. In another embodiment, for example, in the compound of Formula I(a), $R^4$ is H and $R^5$ is $C_{1-6}$ alkyl or $C_{3-8}$ cycloalkyl. In a further embodiment of the present application, for example, in the compound of Formula I(a), $R^4$ is H and $R^5$ is $C_{1-6}$ alkyl. It is an embodiment, for example, in the compound of Formula I(a), that $R^4$ is H and $R^5$ is $C_{3-8}$ cycloalkyl. In another embodiment, for example, in the compound of Formula I(a), $R^4$ is H and $R^5$ is isopropyl. In a further embodiment, for example, in the compound of Formula I(a), $R^4$ is H and $R^5$ is cyclohexyl.

In an embodiment, X is O. In another embodiment, X is S.

In an embodiment, Y is $NR^6$.

In an embodiment, $R^6$ is selected from H, $C_{1-10}$ alkyl, $C_{3-10}$ cycloalkyl, $C_{1-6}$ alkylene $C_{3-10}$ cycloalkyl, heterocycloalkyl and aryl. In another embodiment, $R^6$ is selected from H, $C_{1-6}$ alkyl, $C_{3-8}$ cycloalkyl, $C_{1-4}$ alkylene $C_{3-8}$ cycloalkyl and heterocycloalkyl. In a further embodiment, $R^6$ is H, $C_{1-6}$ alkyl or $C_{3-8}$ cycloalkyl. It is an embodiment that $R^6$ is H. In another embodiment $R^6$ is $C_{1-6}$ alkyl. In another embodiment of the present application, $R^6$ is $C_{3-8}$ cycloalkyl. In a further embodiment, $R^6$ is isopropyl. It is an embodiment that $R^6$ is cyclohexyl.

In an embodiment, Y is $CR^6R^7$.

In an embodiment, $R^6$ and $R^7$ are each independently selected from H, $C_{1-10}$ alkyl, $C_{3-10}$ cycloalkyl, $C_{1-6}$ alkylene $C_{3-10}$ cycloalkyl, heterocycloalkyl and aryl. In another embodiment, $R^6$ and $R^7$ are each independently selected from H, $C_{1-6}$ alkyl, $C_{3-8}$ cycloalkyl, $C_{1-4}$ alkylene $C_{3-8}$ cycloalkyl and heterocycloalkyl. In a further embodiment, $R^6$ and $R^7$ are each independently H, $C_{1-6}$ alkyl or $C_{3-8}$ cycloalkyl.

In an embodiment, the compound of Formula I is a compound of Formula I(a)(i), I(a)(ii), I(a)(iii) or I(a)(iv):

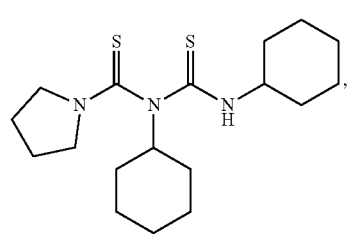

I(a)(i)

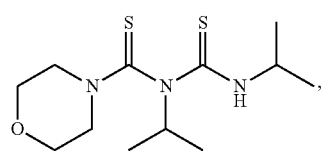

I(a)(ii)

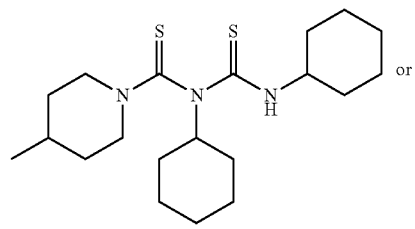

I(a)(iii)

or

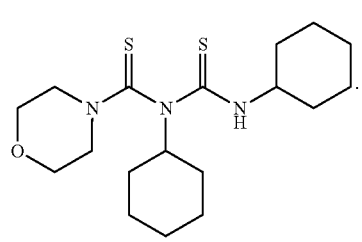

I(a)(iv)

In another embodiment of the present application, the compound of Formula I is the compound of Formula I(a)(i):

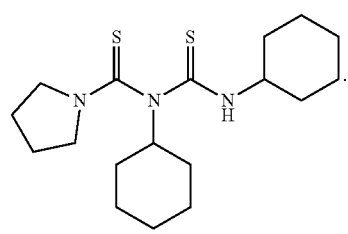

I(a)(i)

In another embodiment of the present application, the compound of Formula I is the compound of Formula I(a)(ii):

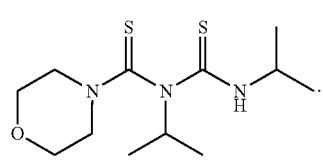

I(a)(ii)

In another embodiment of the present application, the compound of Formula I is the compound of Formula I(a)(iii):

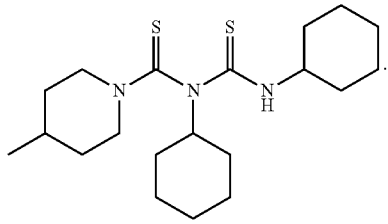

I(a)(iii)

In another embodiment of the present application, the compound of Formula I is the compound of Formula I(a)(iv):

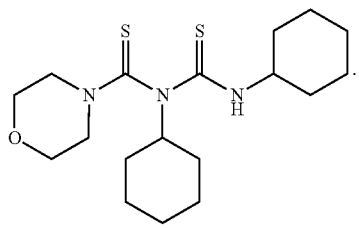

I(a)(iv)

In another embodiment, the compound of Formula I is a compound of Formula I(b)(i):

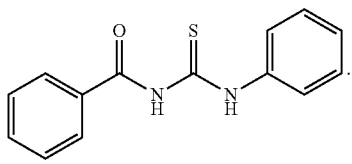

I(b)(i)

In another embodiment, the compound of Formula I is a compound of Formula I(c)(i), I(c)(ii), I(c)(iii) or I(c)(iv):

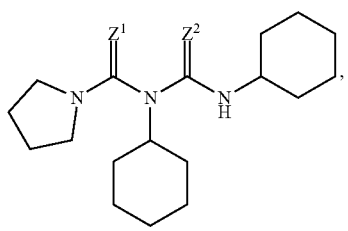

I(c)(i)

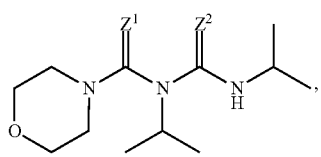

I(c)(ii)

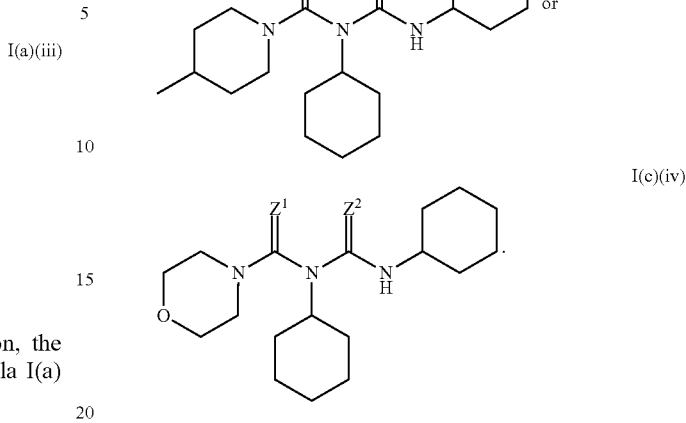

I(c)(iii)

or

I(c)(iv)

wherein in each of the compounds of Formula I(c)(i), I(c)(ii), I(c)(iii) or I(c)(iv) independently, one of $Z^1$ and $Z^2$ is O and the other of $Z^1$ and $Z^2$ is S.

In an embodiment, the molar ratio of the compound of Formula I to the gold and/or palladium is about 1:10 to about 50:1. In another embodiment, the molar ratio of the compound of Formula I to the gold and/or palladium is about 1:1 to about 20:1. In a further embodiment, the molar ratio of the compound of Formula I to the gold and/or palladium is about 2:1 to about 10:1. It is an embodiment that the molar ratio of the compound of Formula I to the gold and/or palladium is about 3:1 to about 4:1. In another embodiment, the molar ratio of the compound of Formula I to the gold and/or palladium is about 3:1. In a further embodiment, the molar ratio of the compound of Formula I to the gold and/or palladium is about 4:1.

The acid can be any suitable acid. In an embodiment, the acid is a hydrogen halide (e.g., HCl, HBr or HI), chlorous acid, chloric acid, bromous acid, bromic acid, iodous acid, iodic acid, perchloric acid, sulfuric acid, nitric acid, oxalic acid, phosphoric acid, an organic acid (e.g., benzenesulfonic acid) or combinations thereof. In another embodiment, the acid is HCl. In another embodiment, the acid is HCl having a concentration in the aqueous solution of about 0.1 M to about 10 M. In a further embodiment, the acid is HCl having a concentration in the aqueous solution of about 0.5 M to about 5 M. It is an embodiment that the acid is HCl having a concentration in the aqueous solution of about 0.75 M to about 3 M. In another embodiment, the acid is HCl having a concentration in the aqueous solution of about 1 M to about 2 M. In a further embodiment, the acid is HCl having a concentration in the aqueous solution of about 1 M. It is an embodiment that the acid is HCl having a concentration in the aqueous solution of about 2 M.

The oxidizing agent can be any suitable oxidizing agent. In an embodiment, the oxidizing agent is ozone, nitric acid ($HNO_3$), hydrogen peroxide ($H_2O_2$), $O_2$, bubbled air, $I_2$, $Br_2$, $Cl_2$, oxone™, an ammonium polyatomic salt (e.g., ammonium chlorite, ammonium periodate ($NH_4IO_3$), ammonium perborate ($NH_4BO_3$), ammonium chlorate ($NH_4ClO_3$), ammonium persulfate ($(NH_4)_2S_2O_8$), ammonium hypochlorite or ammonium nitrate), calcium hypochlorite, a sodium polyatomic salt (e.g., sodium persulfate ($Na_2S_2O_8$), sodium nitrate or sodium hypochlorite), a potassium polyatomic salt (e.g., potassium permanganate, potassium persulfate, potassium iodate, potassium hypochlorite or potassium nitrate), manganese oxide, a tetraalkylammonium salt (e.g., tetramethylammonium chlorite ($N(NH_3)_4)ClO_2$) or tetramethylammonium periodate ($N(NH_3)_4)IO_4$)), peroxomonosulfuric acid, urea, peracetic acid, an alkanesulfonic acid (e.g., methane sulfonic acid), an aromatic sulfonic acid (e.g., benzenesulfonic acid) or combinations thereof.

The oxidizing agent is suitably added to the aqueous phase as an aqueous solution, or if using a gas, is bubbled through the aqueous phase. In another embodiment, the oxidizing agent is $HNO_3$ or $MnO_2$. In another embodiment, the oxidizing agent is $HNO_3$. The concentration of oxidizing agent can be any suitable concentration. For example, above a certain concentration (for example, above about 0.5 M H $NO_3$) the compound of Formula I can be oxidized which reduces the extraction efficiency. In a further embodiment, the oxidizing agent is $HNO_3$ having a concentration in the aqueous solution of about 0.1 M to 2.0 M. In another embodiment, the oxidizing agent is $HNO_3$ having a concentration in the aqueous solution of about 0.1 M to 1.0 M. In another embodiment, the oxidizing agent is $HNO_3$ having a concentration in the aqueous solution of about 0.1 M to 0.5 M. In a further embodiment, the oxidizing agent is $HNO_3$ having a concentration in the aqueous solution of about 0.15 M to 0.25 M.

The water-immiscible organic solvent can be any suitable water-immiscible organic solvent. In an embodiment of the present application, the water-immiscible organic solvent is selected from dichloromethane (DCM), chloroform, dichloroethane, chlorobenzene, dichlorobenzene and toluene. In another embodiment, the water-immiscible organic solvent is selected from dichloromethane, chloroform and chlorobenzene. In a further embodiment, the water-immiscible organic solvent is dichloromethane.

In an embodiment, the conditions to leach the gold and/or palladium from the gold and/or palladium-containing substance and extract the gold and/or palladium by forming a complex between the leached gold and/or palladium and the compound of Formula I in one step, comprise stirring the mixture for a time of about 2 hours to about 10 hours, about 2 hours to about 5 hours, or about 3 hours to about 4 hours at a temperature of about 10° C. to about 40° C. or about 20° C. to about 25° C.

In an embodiment, the method further comprises separating the mixture into an aqueous phase and an organic phase comprising the complex between the leached gold and/or palladium and the compound of Formula I. Methods to separate mixtures comprising an aqueous phase and an organic phase into separate phases are well known in the art and the selection of a suitable method for use in the methods of the present application can be made by a person skilled in the art.

In an embodiment, the method further comprises stripping the gold and/or palladium from the complex between the compound of Formula I and the gold and/or palladium by a method comprising contacting the organic phase with an aqueous solution comprising any suitable acid and thiourea under conditions to obtain a gold and/or palladium-containing strip solution and a gold and/or palladium-reduced organic phase comprising the compound of Formula I. In an embodiment, the conditions to obtain a gold and/or palladium-containing strip solution and a gold and/or palladium-reduced organic phase comprise stirring the organic phase with an aqueous solution comprising $H_2SO_4$, for example 1 M $H_2SO_4$ and thiourea, for example 0.7 M thiourea for a time of about 5 minutes to about 1 hour or about 15 minutes at a temperature of about 10° C. to about 40° C. or about 20° C. to about 25° C. Other suitable acids such as but not limited to HCl may be used in the stripping step. However, it will be appreciated by a person skilled in the art that HCl is corrosive and that HCl gas may come out from the solution during subsequent reduction or electrowinning.

In an embodiment, the method further comprises separating the gold and/or palladium-containing strip solution from the gold and/or palladium-reduced organic phase comprising the compound of Formula I and recovering gold and/or palladium from the gold and/or palladium-containing strip solution by electrowinning or reduction. The gold and/or palladium-containing strip solution and the gold and/or palladium-reduced organic phase comprising the compound of Formula I are separated by any suitable means, the selection of which for use in the methods of the present application can be made by a person skilled in the art.

In an embodiment, the gold and/or palladium is recovered from the gold and/or palladium-containing strip solution by electrowinning.

In another embodiment, the gold and/or palladium is recovered from the gold and/or palladium-containing strip solution by reduction. The reducing agent can be any suitable reducing agent. In an embodiment, the reducing agent is oxalic acid, Zn powder, Fe powder or $NaBH_4$. In an embodiment, the reducing agent is $NaBH_4$ and a temperature of from about 10° C. to about 35° C. or about 20° C. to about 25° C. is used. In another embodiment, the reducing agent is oxalic acid and a temperature of from about 40° C. to about 60° C. or about 50° C. is used.

In another embodiment of the present application, the method further comprises, subsequent to separating the mixture into the aqueous phase and the organic phase, recycling the aqueous phase for use, for example, in the step of contacting the gold and/or palladium-containing substance with the mixture. In another embodiment, the method further comprises, subsequent to stripping and/or direct reduction of gold and/or palladium, for example, with $NaBH_4$ or oxalic acid, recycling the water-immiscible organic solvent from the organic phase for use, for example, in the step of contacting the gold and/or palladium-containing substance with the mixture. In a further embodiment, the method further comprises recycling the compound of Formula I from the gold and/or palladium-reduced organic phase for use, for example, in the step of contacting the gold and/or palladium-containing substance with the mixture.

In an embodiment, the method further comprises recovering gold and/or palladium from the organic phase by direct reduction. The reducing agent can be any suitable reducing agent. In an embodiment, the reducing agent is oxalic acid, Zn powder, Fe powder or $NaBH_4$. In an embodiment, the reducing agent is $NaBH_4$ and a temperature of from about 10° C. to about 35° C. or about 20° C. to about 25° C. is used. In another embodiment, the reducing agent is oxalic acid and a temperature of from about 40° C. to about 60° C. or about 50° C. is used.

The substance comprising gold and/or palladium can be any suitable substance comprising gold and/or palladium. In an embodiment, the substance comprising gold and/or palladium is selected from a gold-containing ore, anode slime, a platinum group metal (PGM)-containing substance such as a PGM concentrate, electronic scrap and jewelry scrap.

In an embodiment, the substance comprising gold and/or palladium is a gold-containing substance. In another embodiment of the present application, the gold-containing substance is a gold-containing ore. In an embodiment, the gold ore is an oxidized gold ore. In another embodiment of the present application, the gold ore is a refractory gold ore.

In an embodiment, the substance comprising gold and/or palladium is a palladium-containing substance. In another embodiment of the present application, the palladium-containing substance is a palladium-containing ore.

In an embodiment, the substance comprising gold and/or palladium is a gold and palladium-containing substance. In another embodiment, the gold and palladium-containing substance is an ore that comprises gold and palladium.

In an embodiment, the substance comprising gold and/or palladium is a platinum group metal-containing substance. In another embodiment, the platinum group metal-containing substance is a platinum group metal concentrate. It will be appreciated by a person skilled in the art that after dissolution of substances containing platinum group metals including platinum, palladium, rhodium, osmium, ruthenium and iridium the compounds of Formula I can selectively extract both palladium and gold into the organic phase and separate them from the rest of the platinum group metals.[44]

[44] Moradi, L. Salimi, H. Piltan, M. Yavari, I. United States Patent. Pub. No. US 2012/0228151 A1. Sep. 13, 2012.

In another embodiment of the present application, the method further comprises crushing and/or grinding the substance comprising gold and/or palladium such as the gold-containing ore into particles prior to contacting with the mixture. In a further embodiment, the size of the particles of the substance comprising gold and/or palladium such as the gold-containing ore is less than or equal to about 75 microns.

In an embodiment, the compounds of Formula I are commercially available or are prepared using methods known in the literature from commercially available materials. For example, a compound of Formula I(a) is prepared by adding an appropriately substituted amine to a mixture of $CS_2$ and a carbodiimide in a suitable polar solvent, such as an alcoholic solvent, under conditions to form the compound of Formula I(a). The compound of Formula I(a) will generally precipitate from the reaction mixture and is isolated and, optionally, purified using known methods. In an embodiment, a slight excess, for example 1.05 to 1.5, suitably 1.1, equivalents of the amine and $CS_2$ are used. In an embodiment, the suitable solvent is methanol or ethanol, suitably methanol. In an embodiment the reaction is performed at or around room temperature, however the temperature can be adjusted as needed by a person skilled in the art.

The present application also includes a use of a compound of Formula I:

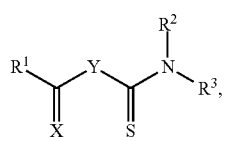

I wherein
R$^1$ is —NR$^4$R$^5$ or aryl;
R$^2$ and R$^3$ are each independently selected from H, C$_{1-10}$ alkyl, C$_{3-10}$ cycloalkyl, C$_{1-6}$ alkylene C$_{3-10}$ cycloalkyl, heterocycloalkyl and aryl; or
R$^2$ and R$^3$ together with the nitrogen atom to which they are attached, form a heterocycloalkyl or a heteroaryl, or a heterocycloalkyl or a heteroaryl substituted at one or more carbon atoms with C$_{1-4}$ alkyl;

R$^4$ and R$^5$ are each independently selected from H, C$_{1-10}$ alkyl, C$_{3-10}$ cycloalkyl, C$_{1-6}$ alkylene C$_{3-10}$ cycloalkyl, heterocycloalkyl and aryl; or
R$^4$ and R$^5$ together with the nitrogen atom to which they are attached, form a heterocycloalkyl or a heteroaryl, or a heterocycloalkyl or a heteroaryl substituted at one or more carbon atoms with C$_{1-4}$ alkyl;
X is O or S;
Y is S, NR$^6$ or CR$^6$R$^7$; and
R$^6$ and R$^7$ are each independently selected from H, C$_{1-10}$ alkyl, C$_{3-10}$ cycloalkyl, C$_{1-6}$ alkylene C$_{3-10}$ cycloalkyl, heterocycloalkyl and aryl, for leaching and extracting gold and/or palladium in one step from a substance comprising gold and/or palladium.

It will be appreciated by a person skilled in the art that the embodiments of the uses for leaching and extracting gold and/or palladium in one step from a substance comprising gold and/or palladium of the present application can be varied as discussed herein for the embodiments of the methods of leaching and extracting gold and/or palladium from a substance comprising gold and/or palladium of the present application.

The following non-limiting examples are illustrative of the present application:

EXAMPLES

Example 1: New Leaching Methods Employing Sulfur-based Ligands for Selective Extraction and Recovery of Gold General Ligand Syntheses The ligands I(a)(i), I(a)(ii), I(a)(iii) and I(a)(iv) (Scheme 2) used in this research were synthesized by following reported literature procedures.[44] The ligand I(b)(i) (N-phenyl-N'-benzoylthiourea) was synthesized based on a reported procedure.[45]

[44] Moradi, L. Salimi, H. Piltan, M. Yavari, I. United States Patent. Pub. No. US 2012/0228151 A1. Sep. 13, 2012.
[45] Vest, P. Schuster, M. Konig, K. H. Fresenius *J Anal Chem.* 1991, 341, 556-568.

For example, for ligands I(a)(i)-I(a)(iv), in a round bottom flask, 1.1 equivalents of a substituted amine was added in small portions over a period of 1 hour to a mixture of 1.3 equivalents of $CS_2$ and 1 equivalent of carbodiimide in methanol at room temperature. The reaction mixture was stirred for 4 hours, and then the resulting white precipitate was separated from the solution by filtration. Finally, it was washed with water and dried under vacuum.

Ligand I(a)(i) Synthesis

In a round bottom flask, 2.02 g pyrrolidine was added in small portions over a period of 1 hour to a mixture of 2.80 g $CS_2$ and 5.85 g of dicyclohexylcarbodiimide (DCC) in 30 ml methanol at room temperature. The reaction mixture was stirred for four hours, and then the resulting white precipitate was separated from the solution by filtration. Finally, it was washed with water and dried under vacuum. 8.93 g final product was isolated (yield: 89%).

Preparation of Gold Powder

Gold powder was prepared by adapting the reported method from Jeffrey et al.[46]. 1.000 g pure (99.9% purity) metallic gold was dissolved in 4 mL aqua regia (3 mL 37%

HCl/1 mL 69% HNO$_3$) and then diluted 5 times by adding distilled water. Sodium metabisulfite was gradually added to the solution while it was being stirred gently. Addition of Na$_2$S$_2$O$_5$ was continued until all of the gold was precipitated out from the solution (the color changed from a yellow to a colorless solution). The resulting precipitate was isolated, washed with 1M HCl and then with distilled water and finally dried in an oven. 0.975 g light brown gold powder was obtained (yield: 97.5%).

[46] Jeffrey, M. Breuer, P. L. Chu, C. K. Int. J. Miner. Process. 2003, 72, 323-330.

(a) Simultaneous Leaching and Solvent Extraction

Effect of HCl Concentration 5.0 mg gold powder (0.025 mmol) was added to a vial containing 5 ml HCl solution with different concentrations (0.1, 0.5, 1, 1.5 and 2M) and 0.22 M HNO$_3$. Then, 26.8 mg (0.075 mmol) ligand I(a)(i) was dissolved in 5 ml dichloromethane and added to the previous solution. The reaction mixture was stirred vigorously for different periods of time. When the reaction was completed, the two phases were separated and the organic phase was stripped with 5 ml H$_2$SO$_4$ (1 M) containing 0.7 M thiourea for 15 min.

The gold content of the strip solutions was analyzed by AAS. Initial investigations (Table 1) showed that there was a significant difference between conventional leaching by HCl/HNO$_3$ versus simultaneous leaching and extraction employing dithiobiuret ligands (entry 3 vs 4). While not wishing to be limited by theory, the initial tiny amount of leached gold is extracted into the organic phase by the sulfur-based ligands, pushing forward the gold leaching equilibrium (Scheme 1) which leads to increased leaching kinetics.

Scheme 1

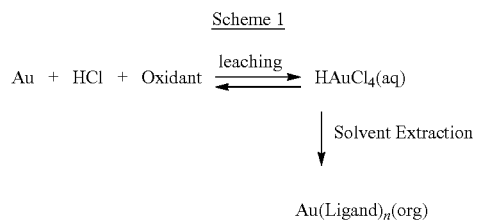

The results showed no significant gold recovery at low HCl concentration (entry 1, 2). However, by increasing HCl concentration gold could be completely recovered at 1 M HCl or higher. As can be seen in table 1, more than 99% recovery was achieved in 4 hours when HCl concentration was 1 M (entry 4), and at higher molarity the recovery time was shorter (entry 5, 6). Therefore, 1 mol/L HCl was chosen as an acid concentration for other experiments.

Figure 2:
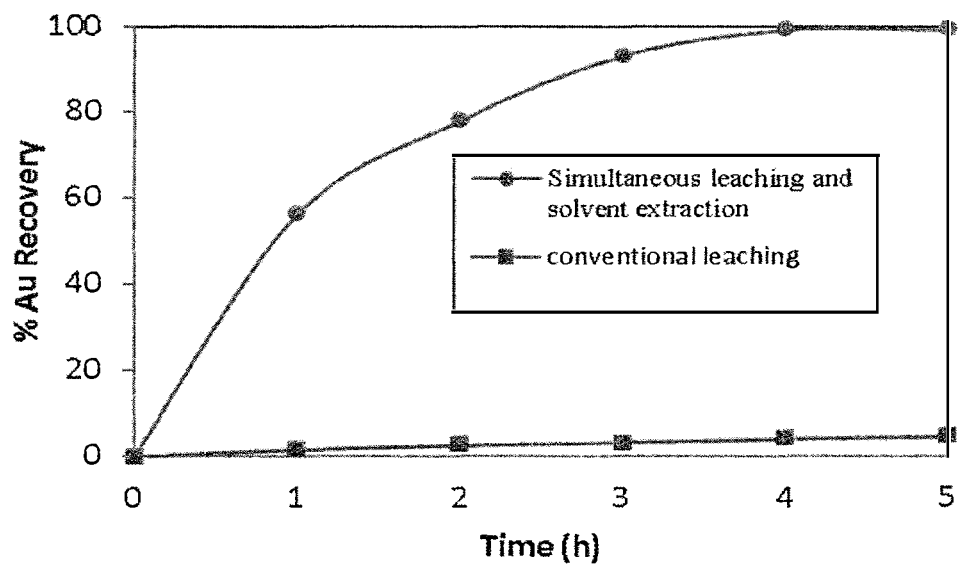
FIG. 2 is a plot showing Au Recovery (%) as a function of time (hours) for simultaneous leaching and extraction according to an embodiment of a method of the present application in comparison to conventional leaching.

Effect of Stirring Time 5.0 mg gold powder (0.025 mmol) was added to a vial containing 5 ml 1 M HCl and 0.22 M HNO$_3$. Then, 26.8 mg (0.075 mmol) ligand I(a)(i) was dissolved in 5 ml dichloromethane and added to the previous solution. The reaction mixture was stirred vigorously for different periods of time. When the reaction was completed, the two phases were separated and the organic phase was stripped with 5 ml H$_2$SO$_4$ (1M) containing 0.7 M thiourea for 15 min. The gold content of the strip solutions was analyzed by AAS. The results obtained (FIG. 2) showed that the gold recovery percentage increased quickly with the simultaneous leaching and extraction system until it reached 99% after 4 hours and remained constant. This is significantly quicker than conventional leaching systems with the same amount of HCl and HNO$_3$. A useful leaching time for Au recovery using the present system was found to be 4 h in 1 M HCl solution.

A comparison of the conventional leaching system to that of the present study shows that the dithiobiuret ligands can efficiently improve the rate of gold leaching with the least amount of acid and oxidizing reagent. In addition to the leaching step, the new technique recovers gold from aqueous solution at the same time; hence the overall time of gold recovery can be much shorter in comparison to cyanide leaching followed by activated carbon adsorption.

Effect of Ligand Concentration 5.0 mg gold powder (0.025 mmol) was added to a vial containing 5 ml 1M HCl and 0.22 M HNO$_3$. Then, different amounts of ligand I(a)(i) (Table 2) were dissolved in 5 ml dichloromethane and added to the previous solution. The reaction mixture was stirred vigorously for 4h. When the reaction was completed, the two phases were separated and the organic phase was stripped with 5 ml H$_2$SO$_4$ (1 M) containing 0.7 M thiourea for 15 min. The gold content of the strip solutions was analyzed by AAS.

Table 2 shows the gold recovery percentage with different ligand to Au ratios. With a 1:1 molar ratio, only 42% of gold was recovered with optimized HCl and oxidant concentrations. Gold recovery increased with increasing ligand concentration in organic solvent and substantially completed at a 3:1 molar ratio (Ligand: Au).

Efficiency of Different Ligand Derivatives

Different derivatives of dithiobiuret ligand (I(a)(i), I(a)(ii), I(a)(iii) and I(a)(iv)) were synthesized and their capabilities were investigated for simultaneous leaching and extraction of gold in HCl media (Scheme 2). Compared to a monodentate thiourea derivative (L$_1$) and conventional gold extractant, dibutylcarbitol (DBC), all of the dithiobiuret derivatives showed a higher percent gold recovery.

Scheme 2

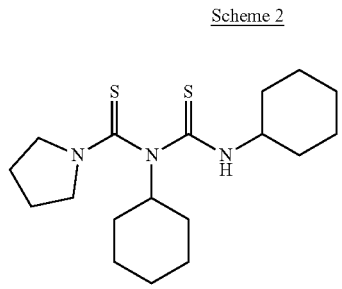

I(a)(i)

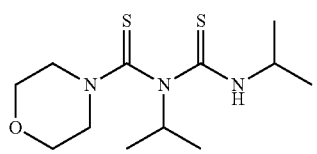

I(a)(ii)

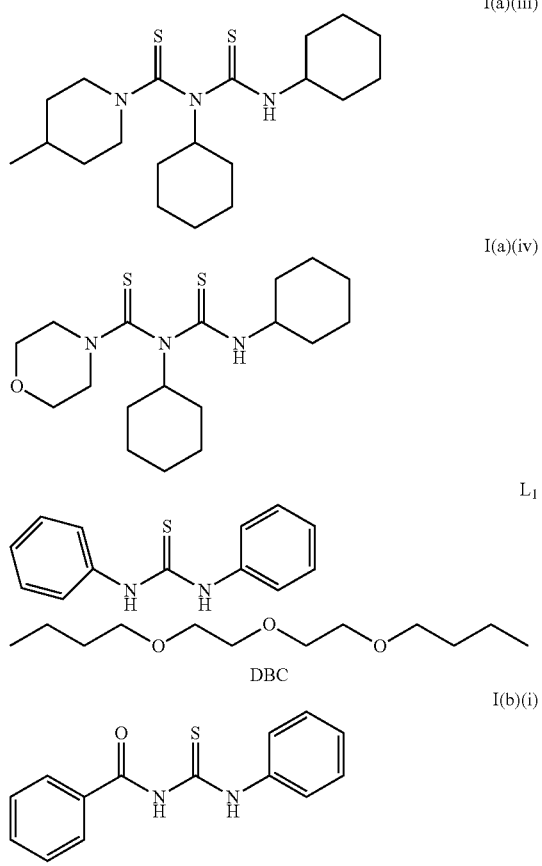

Among the different dithiobiuret derivatives, I(a)(i) showed the highest Au recovery %. DBC is the most common gold extractant which is used for selective extraction of gold from acidic solution. Although it is an effective gold extractant in conventional solvent extraction techniques, it showed very low gold recovery under the present simultaneous leaching and extraction conditions even at extremely high concentrations of extractant (entry 6, Table 3).

The ligand I(b)(i) was also investigated. 5.0 mg gold powder (0.025 mmol) was added to a vial containing 5 ml HCl (1 M) and $HNO_3$ (0.22 M). Then, 20.3 mg (0.075 mmol) of the synthesized ligand I(b)(i) was dissolved in 5 ml dichloromethane and added to the previous solution. The reaction mixture was stirred vigorously for 6 hours. When the reaction was completed, the two phases were separated and the organic phase was stripped with 5 ml $H_2SO_4$ (1 M) containing 0.7 M thiourea for 15 minutes. The gold content of the strip solutions was analyzed by AAS. The results showed that 99.0% of gold was recovered.

Selectivity

To investigate the selectivity of the present technique, a mixture of different metals in chloride form was treated by the system. A mixture of Fe (1000 ppm), Cu (2000 ppm), Zn (500 ppm), Ag (200 ppm) and 0.5 mg gold powder was added to a vial containing 5 ml 1 M HCl and 0.2 M $HNO_3$. Then, 26.8 mg of ligand I(a)(i) was dissolved in 5 ml dichloromethane and added to the previous solution. The reaction mixture was stirred vigorously for different periods of time. When the reaction was completed, the two phases were separated and the organic phase was stripped with 5 ml 1 M $H_2SO_4$ containing 0.7 M thiourea for 15 min. The metal content of the post extraction and strip solutions were analyzed by AAS.

The obtained results, shown in Table 4, demonstrate that the simultaneous leaching and extraction technique employing dithibiuret ligands is highly selective for gold, so that only trace amounts of base metals was extracted even at the presence of high amount of free ligand. In contrast to the cyanidation process, the present technique can, for example eliminate the entire activated carbon step for separation of gold from other impurities.

Effect of Organic Solvent

Simultaneous leaching and extraction tests were performed in the water-immiscible organic solvents shown in Table 5. The results show many organic solvents are suitable for extraction and recovery of gold. Among the investigated solvents, the highest percentages of Au recovery were obtained when dichloromethane (DCM), chlorobenzene, or chloroform were used as solvent.

(b) Gold Ore Treatment

Crushed and ground gold ore with an average gold concentration of 7 ppm and an average particle size of 74 microns was obtained from Claude Resources from their Seabee gold mine operation located in the La Ronge Mining District at the north end of Laonil Lake approximately 125 kilometres northeast of the town of La Ronge, Saskatchewan.

General Experimental For Simultaneous Leaching and Solvent Extraction

Figure 3:
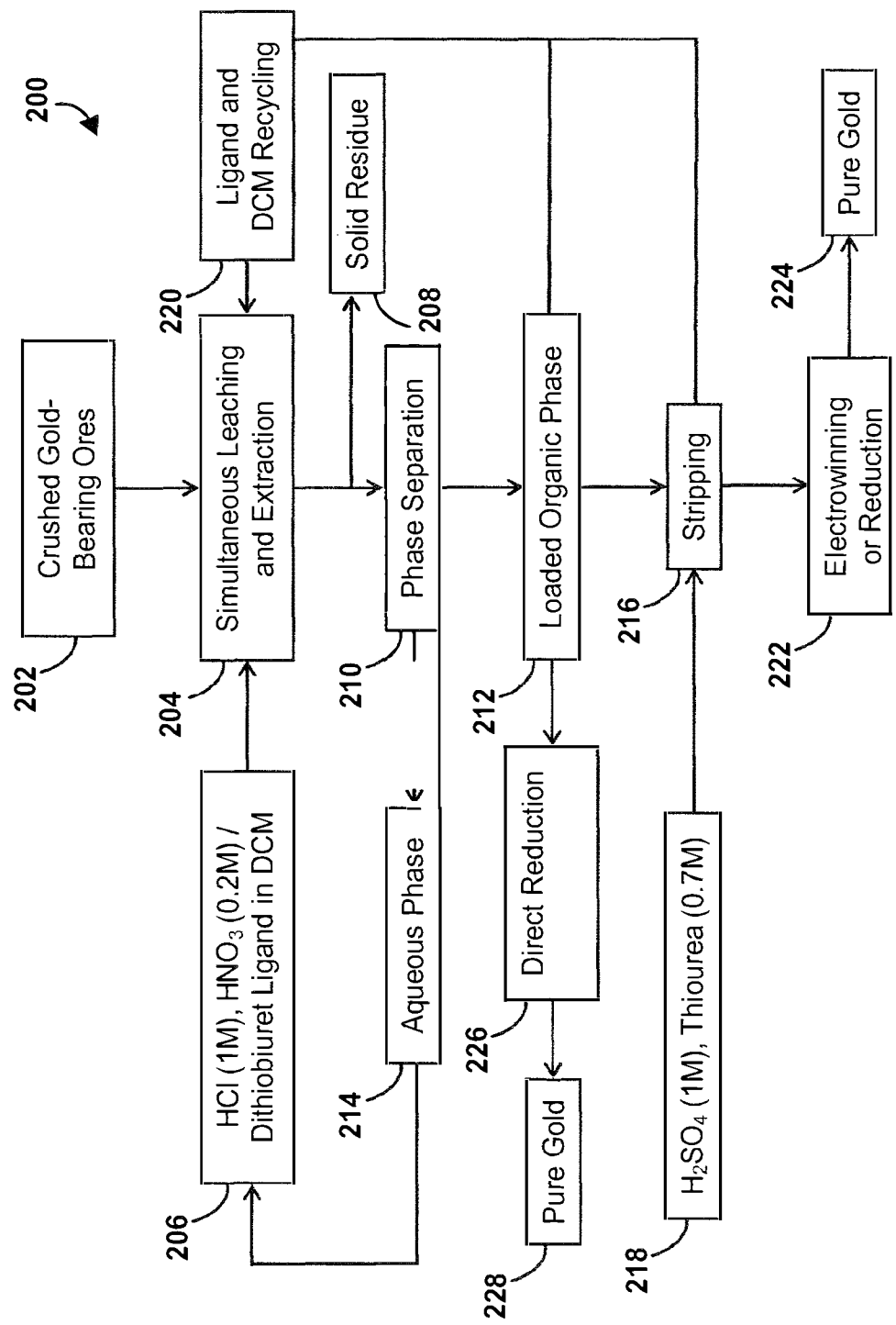
FIG. 3 shows a schematic representation of a method of leaching and extracting gold from a gold-containing substance according to an embodiment of a method of the present application.

A method flow chart for the simultaneous leaching and solvent extraction technique 200 of the present example is shown in FIG. 3. In the method 200, crushed and ground gold ore 202 with an average particle size of 74 microns was subjected to a simultaneous leaching and extracting step 204 wherein the ore 202 was added to a 1 M HCl solution in the presence of $HNO_3$; and a solution of ligand I(a)(i) in dichloromethane was then added to the aqueous solution 206. The resulting biphasic reaction mixture was stirred vigorously for 5 h. The mixture was then filtered to remove solid residue 208 and the phases separated 210 into an organic phase 212 and an aqueous phase 214. The aqueous phase 214 an be recycled for use in the simultaneous leaching and extracting step 204. he organic phase 212 was then stripped 216 with 1 M $H_2SO_4$ containing 0.7 M thiourea 218 for 15 min, and the gold content of the stripped solutions was analyzed by AAS showing gold recovery efficiencies consistently in the 95-97% range. Subsequent to the stripping step 216, the ligand and DCM can be recycled 220 for use in the simultaneous leaching and extraction step 204. An electrowinning or reduction step 222 can be carried out to isolate pure gold 224. Alternatively, instead of stripping step 216, the organic phase 212 can be reduced with an agent such as oxalic acid or $NaBH_4$ 226 to provide pure gold 228. If the organic phase is sensitive to a reducing agent, the use of thiourea stripping 216 of gold from the dithiobiuret gold complex may be used. However, the direct reduction 226 of the loaded organic phase may be more economical. For example, in methods 200 comprising stripping 216 the organic phase, a subsequent electrowinning or reduction step 222 is used to obtain the metallic gold 224 whereas in methods 200 comprising a direct reduction step 226, the metallic gold 228 can be obtained with one less step. In the present experiments, because low concentrations of gold in the samples were used, and the efficiency of the systems was measured, the final gold solutions were analyzed. Instead of weighing the precipitated gold, therefore the organic phase was typically stripped and its gold content measured by AAS.

Exemplary Experimental for Simultaneous Leaching and Solvent Extraction 5.0 g of crushed and ground gold ore with an average particle size of 74 microns was added to a vial containing 5 ml of 1 M HCl and 0.55 M $HNO_3$. 27.8 mg of ligand I(a)(i) dissolved in 5 ml of dichloromethane was then added to the aqueous solution. The reaction mixture was stirred vigorously for 5h. The biphasic reaction mixture was then filtered and the organic phase was isolated. The organic phase was then stripped with 5 ml $H_2SO_4$ (1 M) containing 0.7 M thiourea for 15 min, and the gold content of the stripped solutions was analyzed by AAS. The final solution contained 6.7 ppm gold (96% gold recovery).

(c) Comparative Example: Gold Ore Treatment with Cyanide Solution 5.00 g gold ore was added to a vial containing 10 ml basic solution (pH=10.5, pH was adjusted by dissolving the appropriate amount of KOH in distilled water). 0.20 g KCN was added to the solution and the reaction mixture (open to air) was stirred vigorously for 24 hours. The reaction mixture was weighed before starting and after completion of the reaction to estimate the amount of water evaporated during the leaching process. Then the appropriate amount of water was added to the reaction mixture to keep the slurry's density constant. The gold content of the resultant solution was measured by atomic absorption spectroscopy.

This experiment was conducted to determine the amount of gold in the ore sample and to compare the efficiency of the

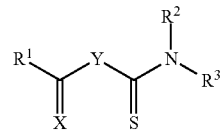

Compounds of Formula I wherein, for example, $R^1$ is $NR^4R^5$; X is S; and Y and $R^2$-$R^5$ are as defined herein are useful for selective extraction of precious metals such as gold from aqueous solutions. Compounds of Formula I wherein, for example, $R^1$ is aryl; X is O; and $R^1$-$R^3$ are as defined herein are also useful for selective extraction of precious metals such as gold from aqueous solution. For example, when X is S, the ligand has two strong donor sites (thiocarbonyl groups) to bind with precious metals which make it a strong bidentate ligand which can form highly stable six-membered ring complexes with precious metals like gold (e.g. compounds of Formula II(a) wherein M comprises a precious metal e.g. Au; and Y and $R^2$-$R^5$ are as defined herein).

[44] Moradi, L. Salimi, H. Piltan, M. Yavari, I. United States Patent. Pub. No. US 2012/0228151 A1. Sep. 13, 2012.

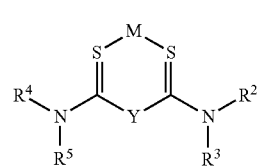

In addition, based on the resonance contributors depicted in Scheme 3, the nitrogen atoms will increase the Lewis basicity at the sulfur atoms, making the sulfur electrons more available to donate to the metal center (further resonance contributors exist when Y=N or S rather than C).

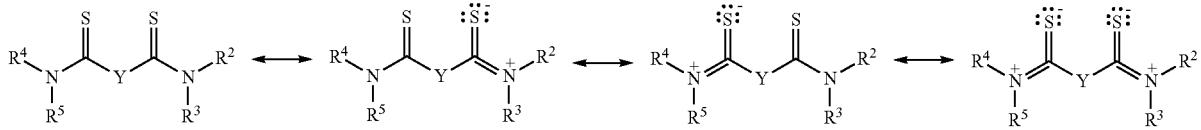

solvent extraction technique of the present studies with the cyanide leaching process. The cyanidation experiment was repeated 20 times on gold ore from the Claude Resources mine, and the results showed the average gold content was between 9.5 and 10 ppm.

(d) Discussion: Solvent Extraction Technique as a Leaching Technique

Appropriate sulfur-containing compounds are useful candidates for gold recovery from ores, because in conformity with Pearson's concept of "hard acid/soft acid and hard base/soft base", precious metals such as gold are typically classified as soft acids while sulfur containing compounds are classified as soft bases. Therefore, appropriate sulfur containing ligands, such as chelating ligands, can be used as highly selective extractants for extraction and recovery of gold[44].

Ligands wherein X=O and $R^1$=aryl behave similarly but were found to take longer to dissolve the gold; e.g. six hours to completely dissolve gold compared to four hours for the dithiobiuret ligands (X=S) studied.

In a typical known solvent extraction process, the desired metal would first be dissolved into water using large amounts of acid in the presence of an oxidant such as hydrogen peroxide or $HNO_3$. In a second step, the metal would then be extracted into an organic phase. Subsequent processing would then usually be required to remove other metal impurities that were also extracted in the process. The solvents would then be removed and the desired metal would be reduced back to its base metal form.

Hydrochloric acid in combination with strong oxidants like $HNO_3$, $H_2O_2$ and $Cl_2$ is a well-known leaching media for gold and other transition metals, but high efficiency is only achieved when high concentrations of acid and oxidant are used. By decreasing the hydrochloric acid concentration in known processes, the leaching kinetic decreases dramatically. However, by keeping the oxidant and HCl concentrations high, their consumption will not be economical and produces a highly corrosive media. In addition, in the case of gold ores, the temperature also is typically increased to obtain an effective leaching. Addition of compounds of Formula I of the application to the leaching media advantageously allows for lower concentrations of acid and oxidant and lower temperatures to be used. Plus, leaching and extraction occur in a single step.

The derivative of dithiobiuret shown in Scheme 4 has been disclosed as a ligand for selective extraction of gold from hydrochloric acid media[44].

Scheme 4

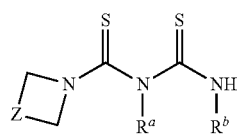

$R^a, R^b$ = cyclohexyl or isopropyl
Z = —CH$_2$—, —CH$_2$CH$_2$—,
—CH$_2$CH$_2$CH$_2$—, —CH$_2$CH(CH$_3$)CH$_2$—,
—CH$_2$(CH$_2$)$_2$CH$_2$—, —CH$_2$NHCH$_2$—,
—CH$_2$CHOHCH$_2$—,
—CHOHCH$_2$CH$_2$—, or —CH$_2$OCH$_2$—

In the present studies, both leaching and extraction steps are done simultaneously under mild conditions which increased the overall efficiencies of the process. As shown in Scheme 1, above, this is accomplished by forcing the reaction equilibrium to the right by withdrawing the dissolved gold from aqueous solution containing small amounts of acid and oxidant into the organic phase containing the ligand. In such a process, highly efficient ligands are used which are able to extract even very small amounts of dissolved gold.

[44] Moradi, L. Salimi, H. Piltan, M. Yavari, I. United States Patent. Pub. No. US 2012/0228151 A1. Sep. 13, 2012.

In known processes, solvent extraction is usually applied after the leaching step. As far as the inventors are aware, performing both steps at the same time to improve the leaching step (as well as overall extraction rates) has never been reported before.

Example 2: Simultaneous Leaching and Solvent Extraction of Palladium 5.0 mg palladium powder (0.047 mmol) was added to a vial containing 5 ml water containing HCl (1M) and HNO$_3$ (0.22 M). Then, 64.95 mg (0.184 mmol) of ligand I(a)(i) was dissolved in 5 ml dichloromethane and added to the previous solution. After 2 hours, the palladium was completely dissolved. The two phases were separated and the organic phase (dark brown) was stripped with 5 ml H$_2$SO$_4$ (1 M) containing 0.7 M thiourea for 15 minutes. Then, the yellow precipitate was filtered off and heated up in a furnace to 700° C. to produce a fine black palladium powder (99.3% of palladium was recovered).

Example 3: Reduction of Leached Gold in Different Organic Solvents

For each test, 5 ml of organic solvent (which contained 0.5 grams of 37% HCl; i.e. the molarity of the HCl in the organic solvent was 1 M) containing different amounts of gold as shown in Table 6 was treated with the indicated reducing reagent for 10 minutes. In the case of Fe powder, the stirring time was 2 hours. The concentration of gold solutions was measured by AAS.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

TABLE 1

Simultaneous leaching and extraction of gold powder in different HCl concentrations.

| Entry | HCl (M) | Time (h) | Au Recovery (%) |
|---|---|---|---|
| 1 | 0.1 | 4 | 5.3 |
| 2 | 0.5 | 4 | 20.7 |
| 3 | 1 | 4 | 4.6* |
| 4 | 1 | 4 | 99.2 |
| 5 | 1.5 | 3 | 99.1 |
| 6 | 2 | 2.5 | 99.3 |

*Conventional leaching by HCl/HNO$_3$.

TABLE 2

Simultaneous leaching and extraction of gold powder with different ligand:Au ratios.

| Entry | Ligand:Au | Au Recovery % |
|---|---|---|
| 1 | 1:1 | 42.7 |
| 2 | 2:1 | 72.4 |
| 3 | 3:1 | 99.5 |
| 4 | 4:1 | 99.4 |

TABLE 3

Simultaneous leaching and extraction of gold powder with different ligands.

| Entry | Ligand | Au Recovery % |
|---|---|---|
| 1 | I(a)(i) | 99.7 |
| 2 | I(a)(ii) | 72.4 |
| 3 | I(a)(iii) | 96.5 |
| 4 | I(a)(iv) | 70.4 |
| 5 | L$_1$ | 3.3 |
| 6 | DBC | 5.1* |

*Pure DBC was used as the organic phase.

TABLE 4

Effect of other impurities on simultaneous leaching and extraction of gold (113 ppm of gold was extracted in the presence of large excesses of Fe, Cu and Zn impurities).

| | Fe | Cu | Zn | Au |
|---|---|---|---|---|
| Aq phase (ppm) | 991.8 | 2140.3 | 542.8 | 0.3 |
| Stripping solution (ppm) | 0.4 | 0.1 | 0.1 | 112.3 |

TABLE 5

Simultaneous leaching and extraction of gold powder in different water-immiscible organic solvents.

| Entry | Solvent | Au Recovery % |
|---|---|---|
| 1 | DCM | 99.9 |
| 2 | Chloroform | 97.4 |
| 3 | Dichloroethane | 68.4 |
| 4 | Chlorobenzene | 98.8 |
| 5 | Dichlorobenzene | 61.3 |
| 6 | Toluene | 56.1 |

TABLE 6

Reduction of leached gold in different organic solvents.

| Entry | Solvent | Reducing agent (mg) | Au concentration before reduction (ppm) | Au concentration after reduction (ppm) | Reduction % |
|---|---|---|---|---|---|
| 1 | Ethyl acetate | Zn powder (20) | 1000 | 5 | 99.5 |
| 2 | Ethyl acetate | Zn powder (10) | 10 | 0 | 100 |
| 3 | Ethyl acetate | NaBH$_4$ (10) | 1000 | 5 | 99.5 |
| 4 | Ethyl acetate | NaBH$_4$ (5) | 10 | 0 | 100 |
| 5 | Ethyl acetate | Fe powder (20) | 1000 | 8 | 99.2 |
| 6 | Ethyl acetate | Fe powder (10) | 10 | 0 | 100 |
| 7 | MeCN | Zn powder (20) | 1000 | 2 | 99.8 |
| 8 | MeCN | Zn powder (10) | 10 | 0 | 100 |
| 9 | MeCN | NaBH$_4$ (10) | 1000 | 6 | 99.4 |
| 10 | MeCN | NaBH$_4$ (5) | 10 | 0.3 | 97.0 |
| 11 | MeCN | Fe powder (20) | 1000 | 12 | 98.8 |
| 12 | MeCN | Fe powder (10) | 10 | 0.1 | 99.0 |
| 13 | CH$_3$COOH | Zn powder (20) | 1000 | 1 | 99.9 |
| 14 | CH$_3$COOH | Zn powder (10) | 10 | 0 | 100 |
| 15 | CH$_3$COOH | NaBH$_4$ (10) | 1000 | 9 | 99.1 |
| 16 | CH$_3$COOH | NaBH$_4$ (5) | 10 | 0 | 100 |
| 17 | CH$_3$COOH | Fe powder (20) | 1000 | 8 | 99.2 |
| 18 | CH$_3$COOH | Fe powder (10) | 10 | 0.5 | 95.0 |

The invention claimed is:

1. A method of leaching and extracting gold and/or palladium from a substance comprising gold and/or palladium, the method comprising:

treating the substance with a mixture comprising an aqueous phase and an organic phase, wherein the aqueous phase comprises an acid and an oxidizing agent, and the organic phase comprises a water-immiscible organic solvent and a compound of Formula I:

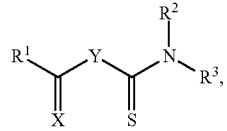

wherein $R^1$ is —$NR^4R^5$ or aryl;

$R^2$ and $R^3$ are each independently selected from H, $C_{1-10}$ alkyl, $C_{3-10}$ cycloalkyl, $C_{1-6}$ alkylene $C_{3-10}$ cycloalkyl, heterocycloalkyl and aryl; or $R^2$ and $R^3$ together with the nitrogen atom to which they are attached, form a heterocycloalkyl or a heteroaryl, or a heterocycloalkyl or a heteroaryl substituted at one or more carbon atoms with $C_{1-4}$ alkyl;

$R^4$ and $R^5$ are each independently selected from H, $C_{1-10}$ alkyl, $C_{3-10}$ cycloalkyl, $C_{1-6}$ alkylene $C_{3-10}$ cycloalkyl, heterocycloalkyl and aryl; or $R^4$ and $R^5$ together with the nitrogen atom to which they are attached, form a heterocycloalkyl or a heteroaryl, or a heterocycloalkyl or a heteroaryl substituted at one or more carbon atoms with $C_{1-4}$alkyl;

X is O or S;

Y is S, $NR^6$ or $CR^6R^7$; and $R^6$ and $R^7$ are each independently selected from H, $C_{1-10}$ alkyl, $C_{3-10}$ cycloalkyl, $C_{1-6}$ alkylene $C_{3-10}$ cycloalkyl, heterocycloalkyl and aryl, and the treating is under conditions to leach the gold and/or palladium from the substance and extract the leached gold and/or palladium by forming a complex between the leached gold and/or palladium and the compound of Formula I, in a single reaction vessel;

wherein the substance is an anode slime, electronic scrap, jewelry scrap, palladium-containing ore, or ore comprising gold and palladium.

2. The method of claim 1, wherein the compound of Formula I is a compound of Formula I(a):

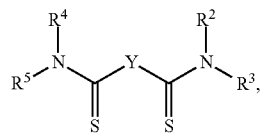

wherein $R^2$, $R^3$, $R^4$, $R^5$ and Y are as defined in claim 1.

3. The method of claim 2, wherein only one of $R^2$, $R^3$, $R^4$ and $R^5$ is H.

4. The method of claim 2, wherein $R^2$ and $R^3$ together with the nitrogen atom to which they are attached form a heterocycloalkyl or a substituted heterocycloalkyl, wherein the heterocycloalkyl is selected from aziridinyl, azetidinyl, pyrrolidinyl, piperidinyl, azepanyl, azocanyl, imidazolidinyl, oxazolidinyl, thiazolidinyl, piperazinyl, hexahydropyrimidinyl, morpholinyl, 1,3-oxazinanyl, thiomorpholinyl, 1,3-thiazinanyl, 1,3-diazepanyl, 1,3-oxazepanyl, 1,3-thiazepanyl, 1,4-diazepanyl, 1,4-oxazepanyl, 1,4-thiazepanyl, 1,3-diazocanyl, 1,3-oxazocanyl, 1,3-thiazocanyl, 1,4-diazocanyl, 1,4-oxazocanyl, 1,4-thiazocanyl, 1,5-diazocanyl, 1,5-oxazocanyl and 1,5-thiazocanyl.

5. The method of claim 4, wherein $R^2$ and $R^3$ together with the nitrogen atom to which they are attached form morpholinyl, pyrrolidinyl or 4-methylpiperidinyl.

6. The method of claim 2, wherein $R^4$ is H and $R^5$ is $C_{1-6}$ alkyl or $C_{3-8}$ cycloalkyl.

7. The method of claim 1, wherein Y is $NR^6$.

8. The method of claim 7, wherein $R^6$ is H, $C_{1-6}$ alkyl or $C_{3-8}$ cycloalkyl.

9. The method of claim 1, wherein the compound of Formula I is a compound of Formula I(a)(i), I(a)(ii), I(a)(iii) or I(a)(iv):

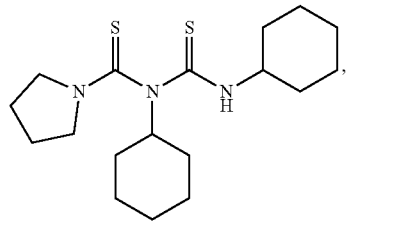
I(a)(i)

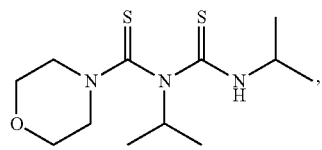
I(a)(ii)

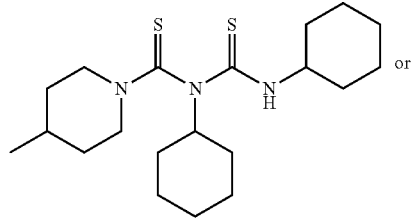
I(a)(iii)
or

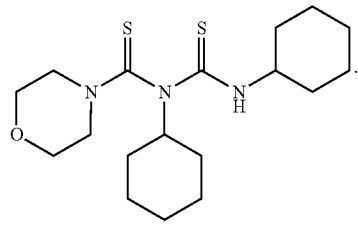
I(a)(iv)

10. The method of claim 9, wherein the compound of Formula I is the compound of Formula I(a)(i):

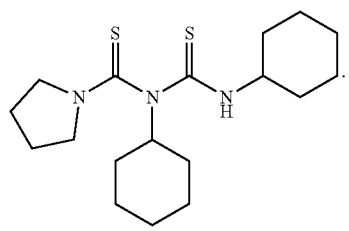
I(a)(i)

11. The method of claim 1, wherein the compound of Formula I is a compound of Formula I(b)(i):

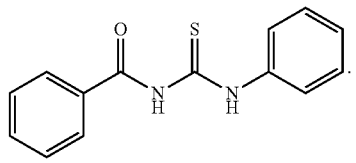
I(b)(i)

12. The method of claim 1, wherein the molar ratio of the compound of Formula I to the gold and/or palladium is about 3:1 to about 4:1.

13. The method of claim 1, wherein the acid in the mixture is a hydrogen halide, chlorous acid, chloric acid, bromous acid, bromic acid, iodous acid, iodic acid, perchloric acid, sulfuric acid, nitric acid, oxalic acid, phosphoric acid, an organic acid, or combinations thereof.

14. The method of claim 13, wherein the acid is selected from HCl, $H_2SO_4$, HBr, $HNO_3$, $H_3PO_4$ and HI.

15. The method of claim 14, wherein the acid is HCl having a concentration in the aqueous solution of about 0.75 M to about 3 M.

16. The method of claim 1, wherein the oxidizing agent is ozone, nitric acid, hydrogen peroxide, $O_2$, bubbled air, $I_2$, $Br_2$, $Cl_2$, potassium monopersulfate, an ammonium polyatomic salt, calcium hypochlorite, a sodium polyatomic salt, a potassium polyatomic salt, manganese oxide, a tetraalkylammonium salt, peroxomonosulfuric acid, urea, peracetic acid, an alkanesulfonic acid, an aromatic sulfonic acid, or combinations thereof.

17. The method of claim 16, wherein the oxidizing agent in the mixture is selected from $HNO_3$, or $MnO_2$.

18. The method of claim 17, wherein the oxidizing agent is $HNO_3$ having a concentration in the aqueous solution of about 0.1 M to 2.0 M.

19. The method of claim 1, wherein the water-immiscible organic solvent is selected from dichloromethane, chloroform and chlorobenzene.

20. The method of claim 1, wherein the conditions to leach the gold and/or palladium from the substance and extract the gold and/or palladium by forming a complex between the leached gold and/or palladium and the compound of Formula I in one step comprise stirring the mixture for a time of about 2 hours to about 10 hours at a temperature of about 10° C. to about 40° C.

21. The method of claim 20, wherein the conditions to leach the gold and/or palladium from the substance and extract the gold and/or palladium by forming a complex between the leached gold and/or palladium and the compound of Formula I in one step comprise stirring the mixture at a temperature of about 20° C. to about 25° C.

22. The method of claim 1, wherein the method further comprises separating the mixture into an aqueous phase and an organic phase comprising the complex between the leached gold and/or palladium and the compound of Formula I.

23. The method of claim 22, wherein the method further comprises stripping the gold and/or palladium from the complex between the compound of Formula I and the leached gold and/or palladium by a method comprising contacting the organic phase with an aqueous solution comprising an acid and thiourea under conditions to obtain a gold and/or palladium-containing strip solution and a gold and/or palladium-reduced organic phase comprising the compound of Formula I.

24. The method of claim 23, wherein the method further comprises separating the gold and/or palladium-containing strip solution from the gold and/or palladium-reduced organic phase comprising the compound of Formula I and recovering gold and/or palladium from the gold and/or palladium-containing strip solution by electrowinning or reduction.

25. The method of claim 23, wherein the method further comprises recycling the compound of Formula I from the gold and/or palladium-reduced organic phase.

26. The method of claim 22, wherein the method further comprises recovering gold and/or palladium from the organic phase by direct reduction.

27. The method of claim 1, wherein the method further comprises, prior to contacting with the mixture, crushing and/or grinding the substance comprising gold and/or palladium into particles.

28. The method of claim 27, wherein the size of the particles of the substance comprising gold and/or palladium is less than or equal to about 75 microns.

\* \* \* \* \*